US012767708B2

(12) United States Patent
Jetha et al.

(10) Patent No.: US 12,767,708 B2
(45) Date of Patent: Oct. 20, 2026

(54) ANTI-PERIOSTIN ANTIBODIES AND USES THEREOF

(71) Applicant: Boehringer Ingelheim IO Canada Inc., Toronto (CA)

(72) Inventors: Arif Jetha, Toronto (CA); Johan Fransson, Toronto (CA); Aj Robert Mcgray, Toronto (CA); Joanne Hulme, Toronto (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1283 days.

(21) Appl. No.: 17/413,094

(22) PCT Filed: Dec. 13, 2019

(86) PCT No.: PCT/IB2019/001307

§ 371 (c)(1),
(2) Date: Jun. 11, 2021

(87) PCT Pub. No.: WO2020/121059

PCT Pub. Date: Jun. 18, 2020

(65) Prior Publication Data

US 2022/0010003 A1 Jan. 13, 2022

Related U.S. Application Data

(60) Provisional application No. 62/899,075, filed on Sep. 11, 2019, provisional application No. 62/779,996, filed on Dec. 14, 2018.

(51) Int. Cl.
*C07K 16/18* (2006.01)
*A61P 35/00* (2006.01)

(52) U.S. Cl.
CPC .............. *C07K 16/18* (2013.01); *A61P 35/00* (2018.01); *C07K 2317/24* (2013.01); *C07K 2317/565* (2013.01); *C07K 2317/76* (2013.01); *C07K 2317/92* (2013.01)

(58) Field of Classification Search
CPC ................ C07K 16/18; C07K 2317/24; C07K 2317/565; C07K 2317/76; C07K 2317/92; C07K 2317/21; C07K 2317/34; C07K 2317/52; C07K 2317/71; C07K 16/46; A61P 35/00; A61K 2039/505; A61K 39/395
See application file for complete search history.

(56) References Cited

U.S. PATENT DOCUMENTS

| | | | |
|---|---|---|---|
| 5,500,362 A | 3/1996 | Robinson et al. |
| 5,624,821 A | 4/1997 | Winter et al. |
| 5,648,260 A | 7/1997 | Winter et al. |
| 5,821,337 A | 10/1998 | Carter et al. |
| 6,602,684 B1 | 8/2003 | Umana et al. |
| 7,087,727 B2 | 8/2006 | Chen et al. |
| 7,371,826 B2 | 5/2008 | Presta |
| 8,017,119 B2 | 9/2011 | Taniyama et al. |
| 8,372,957 B2 | 2/2013 | Taniyama et al. |
| 9,115,190 B2 | 8/2015 | Garnero et al. |
| 9,371,528 B2 | 6/2016 | Stankovic et al. |
| 9,862,762 B2 | 1/2018 | Chowdhury et al. |
| 2005/0014934 A1 | 1/2005 | Hinton et al. |
| 2005/0106644 A1 | 5/2005 | Cairns et al. |
| 2009/0028793 A1 | 1/2009 | Neri et al. |
| 2012/0219977 A1 | 8/2012 | Garnero et al. |
| 2014/0363832 A1 | 12/2014 | Yanagisawa et al. |
| 2014/0377780 A1 | 12/2014 | Neri et al. |
| 2016/0108109 A1 | 4/2016 | Taniyama et al. |
| 2016/0313351 A1 | 10/2016 | Izuhara et al. |
| 2016/0348182 A1 | 12/2016 | Khosravifar et al. |
| 2017/0060482 A1 | 3/2017 | Hara et al. |
| 2017/0290808 A1 | 10/2017 | Charo et al. |
| 2017/0334995 A1 | 11/2017 | Zettl et al. |
| 2020/0239559 A1 | 7/2020 | Weyer-Czernilofsky et al. |
| 2021/0070865 A1 | 3/2021 | Manning et al. |
| 2023/0030597 A1 | 2/2023 | Jetha et al. |

FOREIGN PATENT DOCUMENTS

| | | | |
|---|---|---|---|
| CN | 101389656 A | 3/2009 |
| CN | 103550790 A | 2/2014 |
| CN | 103842823 A | 6/2014 |
| JP | 2009528820 A | 8/2009 |
| JP | 2018536624 A | 12/2018 |
| WO | 199429351 A2 | 12/1994 |
| WO | 2007096142 A2 | 8/2007 |
| WO | 2008077546 A1 | 7/2008 |
| WO | 2015120185 A1 | 8/2015 |
| WO | 2016016265 A1 | 2/2016 |

(Continued)

OTHER PUBLICATIONS

Field et al. Int J Cancer, Novel highly specific anti-periostin antibodies uncover the functional importance of the fascilin 1-1 domain and highlight preferential expression of periostin in aggressive breast cancer, Apr. 15, 2016;138(8):1959-70. doi: 10.1002/ijc. 29946. Epub Dec. 21, (Year: 2015).*
Kudo and Kii, J. Cell Commun. Signal. 12:301-308 (Year: 2018).*
Al-Lazikani, Standard Conformations for the canonical structures of immunoglobulins, J. of MolecularB iology, vol. 273, 1997, 22 pages.
Altschul, Basic Local alignment search tool, J. of Molecular Biol., vol. 2215, 1990, p. 403-410.

(Continued)

*Primary Examiner* — Jeffrey Stucker
*Assistant Examiner* — Sarah Cooper Patterson
(74) *Attorney, Agent, or Firm* — Kenneth J. Kalafus

(57) ABSTRACT

Described herein are antibodies that block the function of periostin. Also described herein are their uses in treating cancer and modifying tumor immune properties.

32 Claims, 13 Drawing Sheets

Specification includes a Sequence Listing.

(56) References Cited

FOREIGN PATENT DOCUMENTS

| | | | | | |
|---|---|---|---|---|---|
| WO | WO-2016068801 | A1 * | 5/2016 | ............. | A61K 35/00 |
| WO | 2017049251 | A2 | 3/2017 | | |
| WO | 2017060482 | A1 | 4/2017 | | |
| WO | 2018030451 | A1 | 2/2018 | | |
| WO | 2018030456 | A1 | 2/2018 | | |
| WO | 2018194134 | A1 | 10/2018 | | |
| WO | 2019063802 | A1 | 4/2019 | | |
| WO | 2020121059 | A1 | 6/2020 | | |
| WO | 2021046634 | A1 | 3/2021 | | |

OTHER PUBLICATIONS

Chowdhury, Engineering hot spots for affinity enhancements of antibodies, Methods in Molecular Biol., vol. 27, 2008, p. 179-196.
Clackson, Making antobidy fragments using phage display libraries, Nature, vol. 352, 1991.
Cunningham, High resolution epitope mapping of hGh-receptor, Science, vol. 244, 1989, 6 pages.
Duncan and Winter, The binding site on Clq on IgG, Nature, vol. 332, 1988, 3 pages.
Edelman, The covalent structure of an entore yG immunoglobulin molecule, Proceedings of the National Academy of Sciences of the US, vol. 63, 1969, p. 78-65.
Field, Novel highly specific anti-periostin antibodies uncover the funactional importance of the fascillin 1-1 domain, Int. J. Cancer, 2016.
Guzik, Development of the inhibitors that target the PD-1/PD-L1 Interaction—A brief look at progress on Small Molecules, Peptides and Macrocycles, Molecules, vol. 24, 2019, p. 1-24.
Honegger, Yet another numbering scheme for immunoglobulin variable domains, Journal of Mole. Biology, vol. 309, 2001, 14 pages.
Hoogenboom, Overview of Antibody-phage Display technology, Methods in Molecular Biology, vol. 178, 2001, 37 pages.
International Preliminary report on Patentability for PCT/CA202/051164 mailed Mar. 24, 2022.
International Search Report and Written Opinion for PCT/CA2020/051164 mailed Oct. 5, 2020.
Kanda, Biotech and Bioengineering, Culture of tomorrow, vol. 94, 2006, p. 680-688.
Karlin and Althshul, Proceedings of the National Academy of Sciences, vol. 87, 1990, 5 pages.
Kindt, Antigens and Antobodies, Kuby Immunology, 2007, p. 91.
Kyutoku, Role of periostin in cancer progression, J. Mole., Med, vol. 28, 2011, 5 pages.
Lefranc, IMGT unique numbering for immunoglobulin and T cell receptor variable domains, Developmental and Comparitve Immunology, vol. 27, 2003, 23 pages.
Li, Cell culture processes for monocolonal antbody production, MABS, Issue 5, 2010, 14 pages.
Liu, Structural characterizations of human periostin, Febs letters, vol. 592, 2018, 15 pages.
Maccallum, Antibody-antigen Interactions, J. of Molecular Biol., vol. 262, 1996, 14 pages.
Meyers, Targeting the PD-1/PD-L1 axis for the treatment of nonn small cell lung cancer, Current Oncology, vol. 25, 2018.
Nakazawa, Periostin blockade overcomes chemoresistance via restricting the expansion of mesenchymal tumor, Scientific Reports, 2017.
Ohnuki, Establishment of FUT8 knockout Chinese hamster ovary Cells, Biotech and Bioengineering, 2004, p. 614.
Okazaki, Fucose Depletion from Human IgG1 Oligosaccharide Enhances Binding Enthalpy and Association, J. of Molecular Biol., vol. 336, 2004, p. 1239-1249.
Parekh, Development and validation of antibody dependent cell-mediated cytotoxicity reporter gene assay, MABS, Issue 3, 2012, 9 pages.
Portolano, Lack of promiscuity in autoantigen-specific H and L chain combinations, J. of Immunology, vol. 150, 1993, 8 pages.
Ripka, Two Chinese Hamster Ovary Glycosylation Mutants affected in the conversion of GDP-Mannose to GDP-Fucose, Archives of Biochem and Biophysics, vol. 249, 1986, p. 533-545.
Wright, Effect of glycosylation on antibody function, Tibtech, vol. 15, 1997, 7 pages.
CAS Registry No. 2249882-54-8, "Ezabenlimab", (2020) SciFinder 3 pgs.
CAT130110187 "Tumor Cell Isolation Kit mouse" Order No. 130-110-187, Miltenyi Biotec, (2020) www.miltenyibiotec.com, 4 pgs.
Fujimura, Taku et al. "Serum levels of soluble CD163 and CXCL5 may be predictive markers for immune-related adverse events in patients with advanced melanoma treated with nivolumab: a pilot study" (2018) Oncotarget, vol. 9, No. 21, 15542-15551.
Kabat et al. "Sequences of proteins of immunological interest", US Department of Heath and Human Services, Public Health Service, 1991, vol. 1, 5th Edition, 25 pgs.
Karlin, Samuel et al. "Applications and statistics for multiple high-scoring segments in molecular sequences" (1993) Proc. Natl. Acad. Sci., vol. 90, 5873-5877.
Li, Yongshu et al. "A Mini-Review for Cancer Immunotherapy: Molecular Understanding of PD-1/PD-L1 Pathway & Translational Blockade of Immune Checkpoints" (2016) International Journal of Molecular Sciences, 17, 1151, 22 pgs.
Field, IJC, Novel highly specific anti-periostin antibodies uncover the functional importance of the fascilin 1-1 domain, vol. 138, 2016.
Kyu, Int. J. of Molecular Med., Role of Periostin in Cancer progression and metastasis, vol. 28, 2011.
International Search Report for PCT/IB2019/001307 mailed Apr. 16, 2020.
Orechhia, EJC, identification of a novel cell binding site of periostin involved in tumour growth, 2011.
Kudo, Akira et al. "Periostin function in communication with extracellular matrices" (2018) J Cell Commun Signal, vol. 12, 301-308.
Abcam Product Datasheet, Anti-Periostin Antibody (EPR20806) ab215199, downloaded Abcam.com, on Mar. 18, 2022, 5 pages.
Kabat, Sequences of Proteins of Immunological Interest, vol. 1, Fifth Edition, 1991, p. 1-25.
Whitelegg, WAM: an improved algorithm for modelling antibodies on the Web, Protein Engineering, 2000, vol. 13, 819-824.
Extended European Search Report for European Application No. 19897138.4, dated Oct. 27, 2022, 7 Pages.
Extended European Search Report for European Application No. 20862817.2, dated Sep. 12, 2023, 10 Pages.
Karlin S., et al., "Methods for Assessing the Statistical Significance of Molecular Sequence Features by Using General Scoring Schemes," Proceedings of the National Academy of Sciences of the United States of America, Mar. 1990, vol. 87, No. 6, pp. 2264-2268.
Paola Orecchia et al.: "Identification of a novel cell binding site of periostin involved in tumour growth", European Journal of Cancer, Elsevier, Amsterdam NL, vol. 47, No. 14, Apr. 19, 2011 (Apr. 19, 2011), pp. 2221-2229, XP028286215, ISSN: 0959-8049, DOI: 10.1016/J.EJCA.2011.04.026 [retrieved on Apr. 26, 2011].

* cited by examiner

ANTI-PERIOSTIN ANTIBODIES AND USES THEREOF

CROSS REFERENCE TO RELATED APPLICATIONS

The present application claims the benefit of U.S. Provisional Application Ser. No. 62/779,996, filed Dec. 14, 2018, and U.S. Provisional Application Ser. No. 62/899,075, filed Sep. 11, 2019, all of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jun. 10, 2021, is named 01-3434-US-3_SL.txt and is 13,226 bytes in size.

BACKGROUND

Periostin (POSTN) is a matricellular protein involved in many physiological processes including epithelial-mesenchymal transition (EMT), cell-matrix interactions and inflammation. POSTN is overexpressed in several pathological contexts, including inflammation, fibrotic diseases and cancer where it correlates with poor prognosis. In cancer, POSTN is typically expressed by stromal cells such as cancer associated fibroblasts (CAFs), however POSTN expression has also been reported in cancer initiating cells (CICs) and MDSCs. POSTN regulates extracellular remodeling by binding other matricellular proteins such as fibronectin and collagen and acts as an integrin receptor ligand to promote cell survival, migration/invasion, EMT, angiogenesis and recruitment of immune cells. POSTN is hypothesized to drive tumor growth and progression by acting on multiple aspects of cancer biology including suppressing anti-tumor immunity by promoting immune exclusion and increasing immunosuppression by tumor infiltrating myeloid cells.

SUMMARY

Described herein are antibodies that inhibit periostin functions, such as integrin mediated cell attachment. Such antibodies are useful for the treatment of cancer. The anti-periostin antibodies described herein decrease the collagen content of tumors, reduce infiltration of suppressive myeloid cell populations, such as granulocytic cells and tumor associated macrophages, while increasing macrophage polarization to an M1 phenotype, and increase the accumulation and anti-tumor properties of tumor infiltrating T cells.

Described herein is a recombinant antibody or antigen binding fragment thereof that binds periostin, wherein the antibody or antigen binding fragment thereof comprises: an immunoglobulin heavy chain CDR1 (CDR-H1) comprising the amino acid sequence set forth in SEQ ID NO: 1 (GYTFTSYG); an immunoglobulin heavy chain CDR2 (CDR-H2) comprising an amino acid sequence set forth in any one of SEQ ID NOs: 2 (ISAYNGNT), 3 (ISAYSGNT), 4 (ISAYQGNT), 5 (ISAYTGNT), or 6 (ISAYDGNT); an immunoglobulin heavy chain CDR3 (CDR-H3) comprising an amino acid sequence set forth in any one of SEQ ID NOs: 7 (DILVVPFDY), 8 (DVLVVPFDY), or 9 (DMLVVPFDY); an immunoglobulin light chain CDR1 (CDR-L1) comprising the amino acid sequence set forth in SEQ ID NO: 10

(SSDIGSNR); an immunoglobulin light chain CDR2 (CDR-L2) amino comprising the amino acid sequence set forth in SEQ ID NO: 11 (SND); and an immunoglobulin light chain CDR3 (CDR-L3) comprising the amino acid sequence set forth in SEQ ID NO: 12 (AAWDDSLSTYV). In some embodiments, the antibody or antigen binding fragment thereof comprises: an immunoglobulin heavy chain CDR1 (CDR-H1) comprising the amino acid sequence set forth in SEQ ID NO: 1 (GYTFTSYG); an immunoglobulin heavy chain CDR2 (CDR-H2) comprising the amino acid sequence set forth in SEQ ID NO: 2 (ISAYNGNT); an immunoglobulin heavy chain CDR3 (CDR-H3) comprising the amino acid sequence set forth in SEQ ID NO: 9 (DMLVVPFDY); an immunoglobulin light chain CDR1 (CDR-L1) comprising the amino acid sequence set forth in SEQ ID NO: 10 (SSDIGSNR); an immunoglobulin light chain CDR2 (CDR-L2) comprising the amino acid sequence set forth in SEQ ID NO: 11 (SND); and an immunoglobulin light chain CDR3 (CDR-L3) comprising the amino acid sequence set forth in SEQ ID NO: 12 (AAWDDSLSTYV). In some embodiments, the recombinant antibody or antigen binding fragment thereof is human, chimeric, or humanized. In some embodiments, the recombinant antibody or antigen binding fragment thereof is an IgG antibody. In certain embodiments, the recombinant antibody or antigen binding fragment thereof comprises one or more mutations to reduce one or more effector functions of the recombinant antibody or antigen binding fragment thereof. In certain embodiments, the one or more mutations to reduce one or more effector functions of the recombinant antibody or antigen binding fragment thereof comprise one or more mutations or sets of mutations selected from: N434A, N434H, T307A/E380A/N434A, M252Y/S254T/T256E, 433K/434F/436H, T250Q, T250F, M428L, M428F, T250Q/M428L, N434S, V308W, V308Y, V308F, M252Y/M428L, D259I/V308F, M428L/V308F, Q311V/N434S, T307Q/N434A, E258F/V427T, S228P, L235E, S228P/L235E/R409K, S228P/L235E, K370Q, K370E, deletion of G446, deletion of K447, and combinations thereof of IgG4 according to the EU numbering system. In certain embodiments, the one or more mutations to reduce one or more effector functions of the recombinant antibody or antigen binding fragment thereof comprise S228P, F234A, and L235A mutations of IgG4 according to the EU numbering system. In some embodiments, the recombinant antibody or antigen binding fragment thereof is a Fab, F(ab)2, a single-domain antibody, or a single chain variable fragment (scFv). In some embodiments, the antibody or antigen binding fragment thereof comprises an immunoglobulin heavy chain variable region and an immunoglobulin light chain variable region: wherein the immunoglobulin heavy chain variable region comprises an amino acid sequence which is at least about 90%, 95%, 97%, 99%, or which is 100% identical to that set forth in SEQ ID NO: 13; and wherein the immunoglobulin light chain variable region comprises an amino acid sequence which is at least about 90%, 95%, 97%, 99%, or which is 100% identical to that set forth in SEQ ID NO: 14, wherein the amino acid at amino acid residue number 55 of SEQ ID NO: 13 is asparagine, serine, glutamine, threonine, or aspartic acid, and wherein the amino acid at amino acid residue number 100 of SEQ ID NO: 13 is methionine, isoleucine, or valine. In some embodiments, the recombinant antibody or antigen binding fragment thereof requires at least one of the following residues: N276, R284, E288, L287, V295, or K302 of SEQ ID NO: 15 for specific binding to periostin. In some embodiments, the recombinant antibody or antigen binding fragment thereof requires at least two, three, four or five of the following residues: N276, R284, E288, L287, V295, or K302 of SEQ ID NO: 15 for specific binding to periostin. In some embodiments, the recombinant antibody or antigen binding fragment thereof requires at least all of the following residues: N276, R284, E288, L287, V295, or K302 of SEQ ID NO: 15 for specific binding to periostin. Also described herein is a pharmaceutical composition comprising the recombinant antibody or antigen binding fragment thereof and a pharmaceutically acceptable excipient, carrier, or diluent. In some embodiments, the pharmaceutical composition is formulated for intravenous administration. In some embodiments, the pharmaceutical composition is formulated for subcutaneous administration. In some embodiments, the pharmaceutical composition is formulated for intratumoral administration. Also described herein is the recombinant antibody or antigen binding fragment thereof or the pharmaceutical composition for use in decreasing collagen content in a tumor. In some embodiments, the recombinant antibody or antigen binding fragment thereof or the pharmaceutical composition is for use in treating cancer. In some embodiments, the cancer comprises glioblastoma, pancreatic cancer, breast cancer, bladder cancer, kidney cancer, head and neck cancer, ovarian cancer, skin cancer, stomach cancer, mesothelioma, liver cancer, endometrial cancer, colon cancer, cervical cancer, prostate cancer, or lung cancer. Also described herein is a method of decreasing collagen content in a tumor in an individual comprising administering to the individual the recombinant antibody or antigen binding fragment thereof or the pharmaceutical composition. Also described herein is a method of increasing M1 macrophage phenotype and/or reducing M2 macrophage phenotype in a tumor in an individual comprising administering to the individual the recombinant antibody or antigen binding fragment thereof or the pharmaceutical composition. Also described herein is a method of reducing accumulation of suppressive granulocytic myeloid cells and/or tumor associated macrophages in an individual comprising administering to the individual the recombinant antibody or antigen binding fragment thereof or the pharmaceutical composition. Also described herein is a method of increasing the frequency of CD4+ and/or CD8+ T cells in a tumor of an individual comprising administering to the individual the recombinant antibody or antigen binding fragment thereof or the pharmaceutical composition. Also described herein is a method of increasing the function of CD8+ T cells in a tumor, measured by interferon gamma expression and/or release by CD8+ T cells in an individual comprising administering to the individual the recombinant antibody or antigen binding fragment thereof or the pharmaceutical composition. Also described herein is a method of treating cancer in an individual comprising administering to the individual a therapeutically effective amount of the recombinant antibody or antigen binding fragment thereof or the pharmaceutical composition. In some embodiments, the cancer comprises glioblastoma, pancreatic cancer, breast cancer, bladder cancer, kidney cancer, head and neck cancer, ovarian cancer, skin cancer, stomach cancer, mesothelioma, liver cancer, endometrial cancer, colon cancer, cervical cancer, prostate cancer, or lung cancer. Also described herein is a method of making composition for decreasing collagen content in a tumor comprising admixing the recombinant antibody or antigen binding fragment thereof and a pharmaceutically acceptable excipient, carrier, or diluent. Also described herein is a method of making composition for increasing M1 macrophage phenotype and/or reducing M2 macrophage phenotype in a tumor comprising admixing the recombinant antibody or antigen binding fragment thereof and a pharmaceutically acceptable excipient, carrier, or diluent. Also described herein is a method of making a composition for reducing accumulation of suppressive granulocytic myeloid cells and/or tumor associated macrophages in an individual comprising admixing the recombinant antibody or antigen binding fragment thereof and a pharmaceutically acceptable excipient, carrier, or diluent. Also described herein is a method of making a composition for increasing the frequency of CD4+ and/or CD8+ T cells in a tumor of an individual comprising admixing the recombinant antibody or antigen binding fragment thereof and a pharmaceutically acceptable excipient, carrier, or diluent. Also described herein is a method of making a composition for increasing the function of CD8+ T cells in a tumor, measured by interferon gamma expression and/or release by CD8+ T cells in an individual comprising admixing the recombinant antibody or antigen binding fragment thereof and a pharmaceutically acceptable excipient, carrier, or diluent. Also described herein is a method of making a composition for treating cancer comprising admixing the recombinant antibody or antigen binding fragment thereof and a pharmaceutically acceptable excipient, carrier, or diluent. In some embodiments, the cancer comprises glioblastoma, pancreatic cancer, breast cancer, bladder cancer, kidney cancer, head and neck cancer, ovarian cancer, skin cancer, stomach cancer, mesothelioma, liver cancer, endometrial cancer, colon cancer, cervical cancer, prostate cancer, or lung cancer.

Also described herein is a recombinant antibody or antigen binding fragment thereof that binds periostin, comprising an immunoglobulin heavy chain variable region and an immunoglobulin light chain variable region: wherein the immunoglobulin heavy chain variable region comprises an amino acid sequence which is at least about 90%, 95%, 97%, 99%, or which is 100% identical to that set forth in SEQ ID NO: 13; and wherein the immunoglobulin light chain variable region comprises an amino acid sequence which is at least about 90%, 95%, 97%, 99%, or which is 100% identical to that set forth in SEQ ID NO: 14, wherein amino acid residue number 55 of SEQ ID NO 13: is asparagine, serine, glutamine, threonine, or aspartic acid, and wherein amino acid residue number 100 of SEQ ID NO: 13 is methionine, isoleucine, or valine. In some embodiments, the recombinant antibody or antigen binding fragment thereof is a human antibody. In some embodiments, the recombinant antibody or antigen binding fragment thereof is an IgG antibody. In certain embodiments, the recombinant antibody or antigen binding fragment thereof comprises one or more mutations to reduce one or more effector functions of the recombinant antibody or antigen binding fragment thereof. In certain embodiments, the one or more mutations to reduce one or more effector functions of the recombinant antibody or antigen binding fragment thereof comprise one or more mutations or sets of mutations selected from: N434A, N434H, T307A/E380A/N434A, M252Y/S254T/T256E, 433K/434F/436H, T250Q, T250F, M428L, M428F, T250Q/M428L, N434S, V308W, V308Y, V308F, M252Y/M428L, D259I/V308F, M428L/V308F, Q311V/N434S, T307Q/N434A, E258F/V427T, S228P, L235E, S228P/L235E/R409K, S228P/L235E, K370Q, K370E, deletion of G446, deletion of K447, and combinations thereof of IgG4 according to the EU numbering system. In certain embodiments, the one or more mutations to reduce one or more effector functions of the recombinant antibody or antigen binding fragment thereof comprise S228P, F234A, and L235A mutations of IgG4 according to the EU numbering system. In some embodiments, the recombinant antibody or antigen binding fragment thereof is a Fab, F(ab)2, a single-domain antibody, or a single chain variable fragment (scFv). Also described herein is a pharmaceutical composition comprising the recombinant antibody or antigen binding fragment thereof and a pharmaceutically acceptable excipient, carrier, or diluent. In some embodiments, the pharmaceutical composition is formulated for intravenous administration. In some embodiments, the pharmaceutical composition is formulated for subcutaneous administration. In some embodiments, the pharmaceutical composition is formulated for intratumoral administration. Also described herein is the recombinant antibody or antigen binding fragment thereof or the pharmaceutical composition for use in decreasing collagen content in a tumor. In some embodiments, the recombinant antibody or antigen binding fragment thereof or the pharmaceutical composition is for use in treating cancer. In some embodiments, the cancer comprises glioblastoma, pancreatic cancer, breast cancer, bladder cancer, kidney cancer, head and neck cancer, ovarian cancer, skin cancer, stomach cancer, mesothelioma, liver cancer, endometrial cancer, colon cancer, cervical cancer, prostate cancer, or lung cancer. Also described herein is a method of decreasing collagen content in a tumor in an individual comprising administering to the individual the recombinant antibody or antigen binding fragment thereof or the pharmaceutical composition. Also described herein is a method of increasing M1 macrophage phenotype and/or reducing M2 macrophage phenotype in a tumor in an individual comprising administering to the individual the recombinant antibody or antigen binding fragment thereof or the pharmaceutical composition. Also described herein is a method of reducing accumulation of suppressive granulocytic myeloid cells and/or tumor associated macrophages in an individual comprising administering to the individual the recombinant antibody or antigen binding fragment thereof or the pharmaceutical composition. Also described herein is a method of increasing the frequency of CD4+ and/or CD8+ T cells in a tumor of an individual comprising administering to the individual the recombinant antibody or antigen binding fragment thereof or the pharmaceutical composition. Also described herein is a method of increasing the function of CD8+ T cells in a tumor, as measured by interferon gamma expression and/or release by CD8+ T cells in an individual comprising administering to the individual the recombinant antibody or antigen binding fragment thereof or the pharmaceutical composition. Also described herein is a method of treating cancer in an individual comprising administering to the individual a therapeutically effective amount of the recombinant antibody or antigen binding fragment thereof or the pharmaceutical composition. In some embodiments, the cancer comprises glioblastoma, pancreatic cancer, breast cancer, bladder cancer, kidney cancer, head and neck cancer, ovarian cancer, skin cancer, stomach cancer, mesothelioma, liver cancer, endometrial cancer, colon cancer, cervical cancer, prostate cancer, or lung cancer. Also described herein is a method of making composition for decreasing collagen content in a tumor comprising admixing the recombinant antibody or antigen binding fragment thereof and a pharmaceutically acceptable excipient, carrier, or diluent. Also described herein is a method of making composition for increasing M1 macrophage phenotype and/or reducing M2 macrophage phenotype in a tumor comprising admixing the recombinant antibody or antigen binding fragment thereof and a pharmaceutically acceptable excipient, carrier, or diluent. Also described herein is a method of making a composition for reducing accumulation of suppressive granulocytic myeloid cells and/or tumor associated macrophages in an individual comprising admixing the recombinant antibody or antigen binding fragment thereof and a pharmaceutically acceptable excipient, carrier, or diluent. Also described herein is a method of making a composition for increasing the frequency of CD4+ and/or CD8+ T cells in a tumor in an individual comprising admixing the recombinant antibody or antigen binding fragment thereof and a pharmaceutically acceptable excipient, carrier, or diluent. Also described herein is a method of making a composition for increasing the function of CD8+ T cells in a tumor, as measured by interferon gamma expression and/or release by CD8+ T cells in an individual comprising admixing the recombinant antibody or antigen binding fragment thereof and a pharmaceutically acceptable excipient, carrier, or diluent. Also described herein is a method of making composition for treating cancer comprising admixing the recombinant antibody or antigen binding fragment thereof and a pharmaceutically acceptable excipient, carrier, or diluent. In some embodiments, the cancer comprises glioblastoma, pancreatic cancer, breast cancer, bladder cancer, kidney cancer, head and neck cancer, ovarian cancer, skin cancer, stomach cancer, mesothelioma, liver cancer, endometrial cancer, colon cancer, cervical cancer, prostate cancer, or lung cancer.

Also described herein is a recombinant antibody or antigen binding fragment thereof that binds periostin, wherein when bound to periostin, the recombinant antibody or antigen binding fragment thereof binds to the Fasciclin 2 (FAS2) domain of periostin. In some embodiments, the recombinant antibody or antigen binding fragment thereof binds to any residue between and including amino acid residues 276 to 302 of periostin (SEQ ID NO: 15). In some embodiments, when bound to periostin, the recombinant antibody or antigen binding fragment thereof binds to at least one of the following residues: N276, R284, E288, L287, V295, or K302 of periostin (SEQ ID NO: 15). In some embodiments, when bound to periostin, the recombinant antibody or antigen binding fragment thereof binds to two, three, four, or five of the following residues: N276, R284, E288, L287, V295, or K302 of periostin (SEQ ID NO: 15). In some embodiments, when bound to periostin, the recombinant antibody or antigen binding fragment thereof binds to all of the following residues: N276, R284, E288, L287, V295, or K302 of periostin (SEQ ID NO: 15). In some embodiments, the antibody or antigen binding fragment thereof comprises an immunoglobulin heavy chain variable region and an immunoglobulin light chain variable region: wherein the immunoglobulin heavy chain variable region comprises an amino acid sequence which is at least about 90%, 95%, 97%, 99%, or which is 100% identical to that set forth in SEQ ID NO: 13; and wherein the immunoglobulin light chain variable region comprises an amino acid sequence which is at least about 90%, 95%, 97%, 99%, or which is 100% identical to that set forth in SEQ ID NO: 14, wherein amino acid residue number 55 of SEQ ID NO: 13 is asparagine, serine, glutamine, threonine, or aspartic acid, and wherein amino acid residue number 100 of SEQ ID NO: 13 is methionine, isoleucine, or valine. In some embodiments, the antibody or antigen binding fragment thereof comprises: an immunoglobulin heavy chain CDR1 (CDR-H1) comprising the amino acid sequence set forth in SEQ ID NO: 1 (GYTFTSYG); an immunoglobulin heavy chain CDR2 (CDR-H2) comprising an amino acid sequence set forth in any one of SEQ ID NOs: 2 (ISAYNGNT), 3 (ISAYSGNT), 4 (ISAYQGNT), 5 (ISAYTGNT), or 6 (ISAYDGNT); an immunoglobulin heavy chain CDR3 (CDR-H3) comprising an amino acid sequence set forth in any one of SEQ ID NOs:

7 (DILVVPFDY), 8 (DVLVVPFDY), or 9 (DMLVVPFDY); an immunoglobulin light chain CDR1 (CDR-L1) comprising the amino acid sequence set forth in SEQ ID NO: 10 (SSDIGSNR); an immunoglobulin light chain CDR2 (CDR-L2) amino comprising the amino acid sequence set forth in SEQ ID NO: 11 (SND); and an immunoglobulin light chain CDR3 (CDR-L3) comprising the amino acid sequence set forth in SEQ ID NO: 12 (AAWDDSLSTYV). In some embodiments, the antibody has an IC50 of less than about 50 nanomolar in a cell adhesion assay performed with human lung fibroblast cells and/or mouse fibroblast cells. Also described herein is a pharmaceutical composition comprising the recombinant antibody or antigen binding fragment thereof and a pharmaceutically acceptable excipient, carrier, or diluent. In some embodiments, the pharmaceutical composition is formulated for intravenous administration. In some embodiments, the pharmaceutical composition is formulated for subcutaneous administration. In some embodiments, the pharmaceutical composition is formulated for intratumoral administration. Also described herein is the recombinant antibody or antigen binding fragment thereof or the pharmaceutical composition for use in decreasing collagen content in a tumor. In some embodiments, the recombinant antibody or antigen binding fragment thereof or the pharmaceutical composition is for use in treating cancer. In some embodiments, the cancer comprises glioblastoma, pancreatic cancer, breast cancer, bladder cancer, kidney cancer, head and neck cancer, ovarian cancer, skin cancer, stomach cancer, mesothelioma, liver cancer, endometrial cancer, colon cancer, cervical cancer, prostate cancer, or lung cancer. Also described herein is a method of decreasing collagen content in a tumor in an individual comprising administering to the individual the recombinant antibody or antigen binding fragment thereof or the pharmaceutical composition. Also described herein is a method of increasing M1 macrophage phenotype and/or reducing M2 macrophage phenotype in a tumor in an individual comprising administering to the individual the recombinant antibody or antigen binding fragment thereof or the pharmaceutical composition. Also described herein is a method of reducing accumulation of suppressive granulocytic myeloid cells and/or tumor associated macrophages in an individual comprising administering to the individual the recombinant antibody or antigen binding fragment thereof or the pharmaceutical composition. Also described herein is a method of increasing the frequency of CD4+ and/or CD8+ T cells in a tumor in an individual comprising administering to the individual the recombinant antibody or antigen binding fragment thereof or the pharmaceutical composition. Also described herein is a method of increasing the function of CD8+ T cells in a tumor, as measured by interferon gamma expression and/or release by CD8+T cells in an individual comprising administering to the individual the recombinant antibody or antigen binding fragment thereof or the pharmaceutical composition. Also described herein is a method of treating cancer in an individual comprising administering to the individual a therapeutically effective amount of the recombinant antibody or antigen binding fragment thereof or the pharmaceutical composition. In some embodiments, the cancer comprises glioblastoma, pancreatic cancer, breast cancer, bladder cancer, kidney cancer, head and neck cancer, ovarian cancer, skin cancer, stomach cancer, mesothelioma, liver cancer, endometrial cancer, colon cancer, cervical cancer, prostate cancer, or lung cancer. Also described herein is a method of making composition for decreasing collagen content in a tumor comprising admixing the recombinant antibody or antigen binding fragment thereof and a pharmaceutically acceptable excipient, carrier, or diluent. Also described herein is a method of making composition for increasing M1 macrophage phenotype and/or reducing M2 macrophage phenotype in a tumor comprising admixing the recombinant antibody or antigen binding fragment thereof and a pharmaceutically acceptable excipient, carrier, or diluent. Also described herein is a method of making a composition for reducing accumulation of suppressive granulocytic myeloid cells and/or tumor associated macrophages in an individual comprising admixing the recombinant antibody or antigen binding fragment thereof and a pharmaceutically acceptable excipient, carrier, or diluent. Also described herein is a method of making a composition for increasing the frequency of CD4+ and/or CD8+ T cells in a tumor of an individual comprising admixing the recombinant antibody or antigen binding fragment thereof and a pharmaceutically acceptable excipient, carrier, or diluent. Also described herein is a method of making a composition for increasing the function of CD8+ T cells in a tumor, as measured by interferon gamma expression and/or release by CD8+ T cells in an individual comprising admixing the recombinant antibody or antigen binding fragment thereof and a pharmaceutically acceptable excipient, carrier, or diluent. Also described herein is a method of making composition for treating cancer comprising admixing the recombinant antibody or antigen binding fragment thereof and a pharmaceutically acceptable excipient, carrier, or diluent. In some embodiments, the cancer comprises glioblastoma, pancreatic cancer, breast cancer, bladder cancer, kidney cancer, head and neck cancer, ovarian cancer, skin cancer, stomach cancer, mesothelioma, liver cancer, endometrial cancer, colon cancer, cervical cancer, prostate cancer, or lung cancer.

Also described herein is a nucleic acid encoding any one of the recombinant antibodies or antigen binding fragments thereof described above.

Also described herein is a cell line comprising the nucleic acid described above. In some embodiments, the cell line is a Chinese Hamster Ovary cell line. Also described herein is a method of producing the recombinant antibody or antigen binding fragment thereof comprising incubating the cell line in a cell culture medium under conditions sufficient to allow expression and secretion of any one of the recombinant antibodies or antigen binding fragments thereof.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIGS. 11A-11C illustrate NB0828 binding to the FAS2 domain of periostin. 11A illustrates NB0828 binding to the chimeric proteins generated in FIG. 10, while FIGS. 11B and 11C illustrate NB0828 binding to alanine mutations in the FAS2 domain of POSTN EMI-FAS4.

DETAILED DESCRIPTION

Figure 1:
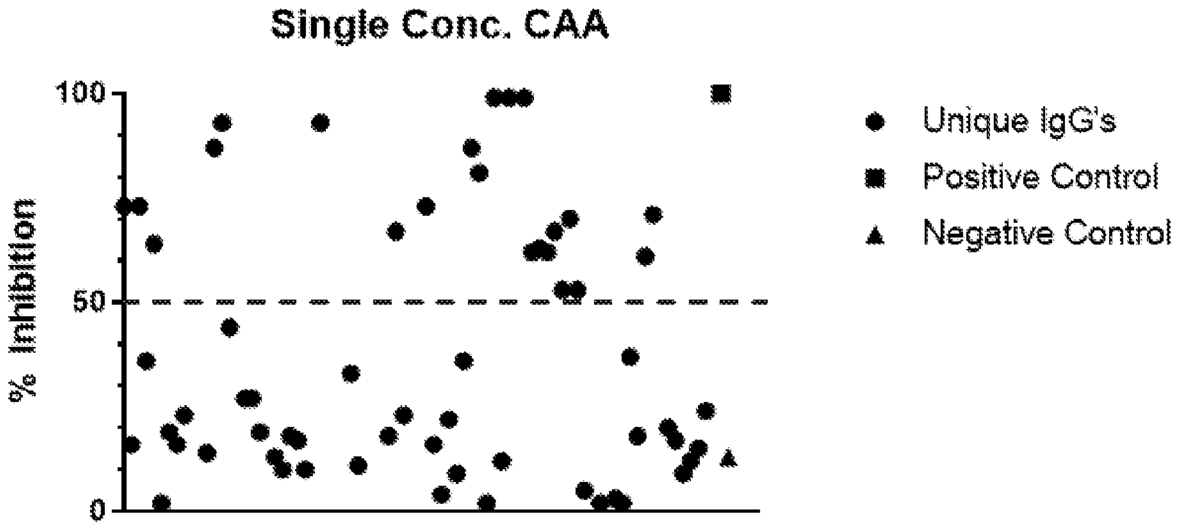
FIG. 1 illustrates inhibition of periostin (POSTN) mediated cell attachment by 78 sequence unique IgGs tested at a single concentration of 500 nM.

Described herein is a recombinant antibody or antigen binding fragment thereof that binds periostin, wherein the antibody or antigen binding fragment thereof comprises: (a) an immunoglobulin heavy chain CDR1 (CDR-H1) comprising the amino acid sequence set forth in SEQ ID NO: 1 (GYTFTSYG); (b) an immunoglobulin heavy chain CDR2 (CDR-H2) comprising an amino acid sequence set forth in any one of SEQ ID NOs: 2 (ISAYNGNT), 3 (ISAYSGNT), 4 (ISAYQGNT), 5 (ISAYTGNT), or 6 (ISAYDGNT); (c) an immunoglobulin heavy chain CDR3 (CDR-H3) comprising an amino acid sequence set forth in any one of SEQ ID NOs: 7 (DILVVPFDY), 8 (DVLVVPFDY), or 9 (DMLVVPFDY); (d) an immunoglobulin light chain CDR1 (CDR-L1) comprising the amino acid sequence set forth in SEQ ID NO: 10 (SSDIGSNR); (e) an immunoglobulin light chain CDR2 (CDR-L2) comprising the amino acid sequence set forth in SEQ ID NO: 11 (SND); and (f) an immunoglobulin light chain CDR3 (CDR-L3) comprising the amino acid sequence set forth in SEQ ID NO: 12 (AAWDDSLSTYV).

Described herein is a recombinant antibody or antigen binding fragment thereof that binds periostin, wherein the antibody or antigen binding fragment thereof comprises any one, two, three, four, five, or six of: (a) an immunoglobulin heavy chain CDR1 (CDR-H1) comprising the amino acid sequence set forth in SEQ ID NO: 1 (GYTFTSYG); (b) an immunoglobulin heavy chain CDR2 (CDR-H2) comprising an amino acid sequence set forth in SEQ ID NO: 16 (ISAYXGNT); (c) an immunoglobulin heavy chain CDR3 (CDR-H3) comprising an amino acid sequence set forth in SEQ ID NO: 17 (DXLVVPFDY); (d) an immunoglobulin light chain CDR1 (CDR-L1) comprising the amino acid sequence set forth in SEQ ID NO: 10 (SSDIGSNR); € an immunoglobulin light chain CDR2 (CDR-L2) comprising the amino acid sequence set forth in SEQ ID NO: 11 (SND); and (f) an immunoglobulin light chain CDR3 (CDR-L3) comprising the amino acid sequence set forth in SEQ ID NO: 12 (AAWDDSLSTYV), wherein X is any amino acid residue.

Described herein is a recombinant antibody or antigen binding fragment thereof that binds periostin, comprising an immunoglobulin heavy chain variable region and an immunoglobulin light chain variable region: (a) wherein the immunoglobulin heavy chain variable region comprises an amino acid sequence which is at least about 90%, 95%, 97%, 99%, or which is 100% identical to that set forth in SEQ ID NO: 13; and (b) wherein the immunoglobulin light chain variable region comprises an amino acid sequence which is at least about 90%, 95%, 97%, 99%, or which is 100% identical to that set forth in SEQ ID NO: 14; wherein amino acid residue number 55 of SEQ ID NO 13: is asparagine, serine, glutamine, threonine, or aspartic acid, or wherein amino acid residue number 100 of SEQ ID NO: 13 is methionine, isoleucine, or valine.

Described herein is a recombinant antibody or antigen binding fragment thereof that binds periostin, comprising an immunoglobulin heavy chain variable region and an immunoglobulin light chain variable region: (a) wherein the immunoglobulin heavy chain variable region comprises an amino acid sequence which is at least about 90%, 95%, 97%, 99%, or which is 100% identical to that set forth in SEQ ID NO: 13; and (b) wherein the immunoglobulin light chain variable region comprises an amino acid sequence which is at least about 90%, 95%, 97%, 99%, or which is 100% identical to that set forth in SEQ ID NO: 14.

Described herein is a recombinant antibody or antigen binding fragment thereof that binds periostin, comprising an immunoglobulin heavy chain variable region and an immunoglobulin light chain variable region: (a) wherein the immunoglobulin heavy chain variable region comprises an amino acid sequence identical to that set forth in SEQ ID NO: 13; and (b) wherein the immunoglobulin light chain variable region comprises an amino acid sequence identical to that set forth in SEQ ID NO: 14.

Described herein is a recombinant antibody or antigen binding fragment thereof that binds to the Fasciclin 2 (FAS2) domain of periostin. In certain embodiments, the recombinant antibody or antigen binding fragment thereof when bound to periostin contacts an amino acid residue selected from amino acid 276 to 302 of SEQ ID NO: 15. In certain embodiments, the recombinant antibody or antigen binding fragment thereof when bound to periostin contacts one of the following amino acid residues: N276, R284, E288, L287, V295, or K302 and SEQ ID NO: 15.

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein the term "about" refers to an amount that is near the stated amount by 10% or less.

As used herein the term "individual," "patient," or "subject" refers to individuals diagnosed with, suspected of being afflicted with, or at-risk of developing at least one disease for which the described compositions and method are useful for treating. In certain embodiments, the individual is a mammal. In certain embodiments, the mammal is a mouse, rat, rabbit, dog, cat, horse, cow, sheep, pig, goat, llama, alpaca, or yak. In certain embodiments, the individual is a human.

As used herein the term "treat" or "treating" refers to interventions to a physiological or disease state of an individual designed or intended to ameliorate at least one sign or symptom associated with said physiological or disease state. The skilled artisan will recognize that given a heterogeneous population of individuals afflicted with a disease, not all individuals will respond equally, or at all, to a given treatment. Individuals are considered to be treated regardless of any objective response criteria.

Among the provided antibodies are monoclonal antibodies, polyclonal antibodies, multispecific antibodies (for example, bispecific antibodies and polyreactive antibodies), and antibody fragments. The antibodies include antibody-conjugates and molecules comprising the antibodies, such as chimeric molecules. Thus, an antibody includes, but is not limited to, full-length and native antibodies, as well as fragments and portions thereof retaining the binding specificities thereof, such as any specific binding portion thereof including those having any number of, immunoglobulin classes and/or isotypes (e.g., IgG1, IgG2, IgG3, IgG4, IgA, IgD, IgE and IgM); and biologically relevant (antigen-binding) fragments or specific binding portions thereof, including but not limited to Fab, F(ab')2, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. A polyclonal antibody is a preparation that includes different antibodies of varying sequences that generally are directed against two or more different determinants (epitopes). The monoclonal antibody can comprise a human IgG1 constant region. The monoclonal antibody can comprise a human IgG4 constant region.

The term "antibody" herein is used in the broadest sense and includes polyclonal and monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD. The antibody can comprise a human IgG1 constant region. The antibody can comprise a human IgG4 constant region.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273, 927-948 ("Chothia" numbering scheme); MacCallum et al., *J. Mol. Biol.* 262:732-745 (1996), "Antibody-antigen interactions: Contact analysis and binding site topography," *J. Mol. Biol.* 262, 732-745. ("Contact" numbering scheme); Lefranc M P et al., "IMGT unique numbering for immunoglobulin and T cell receptor variable domains and Ig superfamily V-like domains," Dev Comp *Immunol,* 2003 January; 27(1):55-77 ("IMGT" numbering scheme); Honegger A and Plückthun A, "Yet another numbering scheme for immunoglobulin variable domains: an automatic modeling and analysis tool," *J Mol Biol,* 2001 Jun. 8; 309(3):657-70, ("Aho" numbering scheme); and Whitelegg N R and Rees A R, "WAM: an improved algorithm for modelling antibodies on the WEB," *Protein Eng.* 2000 December; 13(12):819-24 ("AbM" numbering scheme.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs (See e.g., Kindt et al. Kuby *Immunology,* 6th ed., W.H. Freeman and Co., page 91(2007)). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (See e.g., Portolano et al., *J Immunol.* 150:880-887 (1993); Clarkson et al., *Nature* 352:624-628 (1991)).

Among the provided antibodies are antibody fragments. An "antibody fragment" refers to a molecule other than an intact antibody that comprises a portion of an intact antibody that binds the antigen to which the intact antibody binds. Examples of antibody fragments include, but are not limited to, Fv, Fab, Fab', Fab'-SH, $F(ab')_2$; diabodies; linear antibodies; single-chain antibody molecules (e.g. scFv or sFv); and multispecific antibodies formed from antibody fragments. In particular embodiments, the antibodies are single-chain antibody fragments comprising a variable heavy chain region and/or a variable light chain region, such as scFvs.

The term "specific binding" or "binding" when used herein refers to binding mediated by one or more amino acid residues of the CDR of the antibody or fragment referred to, or one or more variable region amino acid residues of the antibody or fragment referred to. As used herein the term "contact" or "contacts" in reference to an antibody binding or being bound to a specific target refers to an amino acid residue of variable region or a CDR coming within 5, 4, 3 or fewer angstroms of the recited contacted residue. Contact includes hydrogen bonding, Van der Waal's interactions and salt bridge formation between an amino acid residue of the variable region or CDR of the antibody and the recited residue.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., polypeptide linkers, and/or those that are not produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived or selected from human antibody libraries, including phage display and cell-free libraries, containing antibody-encoding sequences derived from a human repertoire. In certain embodiments, a human antibody can have sequence liabilities removed or its affinity increased by successive rounds of selection by a method such as phage display.

The terms "polypeptide" and "protein" are used interchangeably to refer to a polymer of amino acid residues and are not limited to a minimum length. Polypeptides, including the provided antibodies and antibody chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

Provided herein, in certain embodiments, are antibodies with reduced effector function. The phrase "effector function" as used herein, is intended to include the functional capabilities imparted by an Fc-containing protein upon binding to an FcγR. Without being bound to any one theory, formation of an Fc/FcγR complex recruits a variety of effector cells to sites of bound antigen, typically resulting in diverse signaling events within the cells and important subsequent immune responses. Effector function refers to both antibody-dependent cellular cytotoxicity and complement dependent cytotoxicity. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity) but retains FcRn binding ability. Non-limiting examples of in vitro assays to assess ADCC activity of a molecule of interest are described in U.S. Pat. Nos. 5,500,362 and 5,821,337. Alternatively, non-radioactive assays methods may be employed (e.g., ACTI™ and CytoTox 96® non-radioactive cytotoxicity assays). Useful effector cells for such assays include peripheral blood mononuclear cells (PBMC), monocytes, macrophages, and Natural Killer (NK) cells.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In some embodiments, amino acid sequence variants of the antibodies provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of known techniques. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants having one or more amino acid substitutions are provided. Sites of interest for mutagenesis by substitution include the CDRs and FRs. Amino acid substitutions may be introduced into an antibody of interest and the products screened for a desired activity, e.g., retained/improved antigen binding, decreased immunogenicity, or improved ADCC or CDC.

In some embodiments, substitutions, insertions, or deletions may occur within one or more CDRs, wherein the substitutions, insertions, or deletions do not substantially reduce antibody binding to antigen. For example, conservative substitutions that do not substantially reduce binding affinity may be made in CDRs. Such alterations may be outside of CDR "hotspots." In some embodiments of the variant $V_H$ and $V_L$ sequences, each CDR is unaltered.

Alterations (e.g., substitutions) may be made in CDRs, e.g., to improve antibody affinity. Such alterations may be made in CDR encoding codons with a high mutation rate during somatic maturation (See e.g., Chowdhury, *Methods Mol. Biol.* 207:179-196 (2008)), and the resulting variant can be tested for binding affinity. Affinity maturation (e.g., using error-prone PCR, chain shuffling, randomization of CDRs, or oligonucleotide-directed mutagenesis) can be used to improve antibody affinity (See e.g., Hoogenboom et al. in *Methods in Molecular Biology* 178:1-37 (2001)). CDR residues involved in antigen binding may be specifically identified, e.g., using alanine scanning mutagenesis or modeling (See e.g., Cunningham and Wells Science, 244:1081-1085 (1989)). CDR-H3 and CDR-L3 in particular are often targeted. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions and deletions include amino- and/or carboxyl-terminal fusions ranging in length from one residue to polypeptides containing a hundred or more residues, as well as intrasequence insertions and deletions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody. Examples of intrasequence insertion variants of the antibody molecules include an insertion of 3 amino acids in the light chain. Examples of terminal deletions include an antibody with a deletion of 7 or less amino acids at an end of the light chain.

In some embodiments, the antibodies are altered to increase or decrease their glycosylation (e.g., by altering the amino acid sequence such that one or more glycosylation sites are created or removed). A carbohydrate attached to an Fc region of an antibody may be altered. Native antibodies from mammalian cells typically comprise a branched, biantennary oligosaccharide attached by an N-linkage to $Asn_{297}$ of the CH2 domain of the Fc region (See e.g., Wright et al. *TIBTECH* 15:26-32 (1997)). The oligosaccharide can be various carbohydrates, e.g., mannose, N-acetyl glucosamine (GlcNAc), galactose, sialic acid, fucose attached to a GlcNAc in the stem of the biantennar oligosaccharide structure. Modifications of the oligosaccharide in an antibody can be made, for example, to create antibody variants with certain improved properties. Antibody glycosylation variants can have improved ADCC and/or CDC function. In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at $Asn_{297}$, relative to the sum of all glycostructures attached to Asn297 (See e.g., WO 08/077546). $Asn_{297}$ refers to the asparagine residue located at about position 297 in the Fc region (EU numbering of Fc region residues; See e.g., Edelman et al. *Proc Natl Acad Sci*

*USA*. 1969 May; 63(1):78-85). However, $Asn_{297}$ may also be located about ±3 amino acids upstream or downstream of position 297, i.e., between positions 294 and 300, due to minor sequence variations in antibodies. Such fucosylation variants can have improved ADCC function (See e.g., Okazaki et al. J. Mol. Biol. 336:1239-1249 (2004); and Yamane-Ohnuki et al. *Biotech. Bioeng.* 87: 614 (2004)). Cell lines, e.g., knockout cell lines and methods of their use can be used to produce defucosylated antibodies, e.g., Lec13 CHO cells deficient in protein fucosylation and alpha-1,6-fucosyltransferase gene (FUT8) knockout CHO cells (See e.g., Ripka et al. *Arch. Biochem. Biophys.* 249:533-545 (1986); Yamane-Ohnuki et al. *Biotech. Bioeng.* 87: 614 (2004); Kanda, Y. et al., *Biotechnol. Bioeng.,* 94(4):680-688 (2006)). Other antibody glycosylation variants are also included (See e.g., U.S. Pat. No. 6,602,684).

In some embodiments, one or more amino acid modifications may be introduced into the Fc region of an antibody provided herein, thereby generating an Fc region variant. An Fc region herein is a C-terminal region of an immunoglobulin heavy chain that contains at least a portion of the constant region. An Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution) at one or more amino acid positions.

Antibodies can have increased half-lives and improved binding to the neonatal Fc receptor (FcRn) (See e.g., US 2005/0014934). Such antibodies can comprise an Fc region with one or more substitutions therein which improve binding of the Fc region to FcRn, and include those with substitutions at one or more of Fc region residues: 238, 256, 265, 272, 286, 303, 305, 307, 311, 312, 317, 340, 356, 360, 362, 376, 378, 380, 382, 413, 424 or 434 according to the EU numbering system (See e.g., U.S. Pat. No. 7,371,826). Other examples of Fc region variants are also contemplated (See e.g., Duncan & Winter, *Nature* 322:738-40 (1988); U.S. Pat. Nos. 5,648,260 and 5,624,821; and WO94/29351).

In some embodiments, it may be desirable to create cysteine engineered antibodies, e.g., "thioMAbs," in which one or more residues of an antibody are substituted with cysteine residues. In some embodiments, the substituted residues occur at accessible sites of the antibody. Reactive thiol groups can be positioned at sites for conjugation to other moieties, such as drug moieties or linker drug moieties, to create an immunoconjugate. In some embodiments, any one or more of the following residues may be substituted with cysteine: V205 (Kabat numbering) of the light chain; A118 (EU numbering) of the heavy chain; and S400 (EU numbering) of the heavy chain Fc region.

In some embodiments, an antibody provided herein may be further modified to contain additional nonproteinaceous moieties that are known and available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n vinyl pyrrolidone)polyethylene glycol, polypropylene glycol homopolymers, polypropylen oxide/ethylene oxide co-polymers, polyoxyethylated polyols (e.g., glycerol), polyvinyl alcohol, and mixtures thereof. Polyethylene glycol propionaldehyde may have advantages in manufacturing due toits stability in water. The polymer may be of any molecular weight, and may be branched or unbranched. The number of polymers attached to the antibody may vary, and if two or more polymers are attached, they can be the same or different molecules.

The antibodies described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

As used herein, the terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

The nucleic acids encoding the antibodies described herein can be used to infect, transfect, transform, or otherwise render a suitable cell transgenic for the nucleic acid, thus enabling the production of antibodies for commercial or therapeutic uses. Standard cell lines and methods for the production of antibodies from a large-scale cell culture are known in the art. See e.g., Li et al., "Cell culture processes for monoclonal antibody production." *Mabs.* 2010 September-October; 2(5): 466-477. In certain embodiments, the cell is a Eukaryotic cell. In certain embodiments, the Eukaryotic cell is a mammalian cell. In certain embodiments, the mammalian cell is a Chines Hamster Ovary cell (CHO) cell, an NS0 murine myeloma cell, or a PER.C6® cell. In certain embodiments, the nucleic acid encoding the antibody is integrated into a genomic locus of a cell useful for producing antibodies. In certain embodiments, described herein is a method of making an antibody comprising culturing a cell comprising a nucleic acid encoding an antibody under conditions in vitro sufficient to allow production and secretion of said antibody.

In certain embodiments, described herein, is a master cell bank comprising: (a) a mammalian cell line comprising one or more nucleic acids encoding an antibody described herein integrated at a genomic location; and (b) a cryoprotectant. In certain embodiments, the cryoprotectant comprises glycerol, DMSO, or a combination thereof. In certain embodiments, the master cell bank comprises: (a) a CHO cell line comprising a nucleic acid encoding an antibody with (i) a heavy chain amino acid sequence at least 90% identical to that set forth by SEQ ID NO: 13; and (ii) a light chain amino acid sequence at least 90% identical to that set forth by SEQ ID NO: 14 integrated at a genomic location; and (b) a cryoprotectant. In certain embodiments, the cryoprotectant comprises glycerol, DMSO, or a combination thereof. In certain embodiments, the master cell bank is contained in a suitable vial or container able to withstand freezing by liquid nitrogen.

Also described herein are methods of making an antibody described herein. Such methods comprise incubating a cell or cell-line comprising a nucleic acid encoding the antibody in a cell culture medium under conditions sufficient to allow for expression and secretion of the antibody, and further harvesting the antibody from the cell culture medium. The harvesting can further comprise one or more purification steps to remove live cells, cellular debris, non-antibody proteins or polypeptides, undesired salts, buffers, and medium components. In certain embodiments, the additional purification step(s) include centrifugation, ultracentrifugation, dialysis, desalting, protein A, protein G, protein A/G, or protein L purification, and/or ion exchange chromatography.

Anti-Periostin Antibodies

Described herein are antibodies that inhibit periostin (POSTN) function. Such antibodies are useful for the treatment of cancer. The antibodies described herein decrease the collagen content of tumors, reduce infiltration of granulocytes and tumor associated macrophages while increasing macrophage polarization to an M1 phenotype, and increase the accumulation and anti-tumor properties of tumor infiltrating T cells. In certain embodiments, the anti-periostin antibodies decrease tumor collagen content by at least about 5%, 10%, 15%, 20%, 25%, 30%, 35%, or 40% compared to no treatment or control treatment. In certain embodiments, the anti-periostin antibodies reduce infiltration of granulocytes and tumor associated macrophages by at least about 20%, 25%, 30%, 35%, 40%, 45%, or 50% compared to no treatment or control treatment. In certain embodiments, the anti-periostin antibodies reduce infiltration of CD11b+ cells by at least about 20%, 25%, 30%, 35%, 40%, 45%, or 50% compared to no treatment or control treatment. In certain embodiments, the anti-periostin antibodies increase polarization of tumor associated macrophages to the M1 type (CD11b+, MHC class II+, CD206−) by at least about 20%, 25%, 30%, 35%, 40%, 45%, or 50% compared to no treatment or control treatment. In certain embodiments, the anti-periostin antibodies increase accumulation of CD4+ and/or CD8+ T cells in a tumor by at least about 20%, 25%, 30%, 35%, 40%, 45%, or 50% compared to no treatment or control treatment. In certain embodiments, the anti-periostin antibodies increase production of interferon gamma of tumor infiltrating CD8+ T cells by at least about 20%, 25%, 30%, 35%, 40%, 45%, or 50% compared to no treatment or control treatment.

Described herein is a recombinant antibody or antigen binding fragment thereof that binds periostin, wherein the antibody or antigen binding fragment thereof comprises: (a) an immunoglobulin heavy chain CDR1 (CDR-H1) comprising the amino acid sequence set forth in SEQ ID NO: 1 (GYTFTSYG); (b) an immunoglobulin heavy chain CDR2 (CDR-H2) comprising an amino acid sequence set forth in SEQ ID NO: 16 (ISAYXGNT); (c) an immunoglobulin heavy chain CDR3 (CDR-H3) comprising an amino acid sequence set forth in SEQ ID NO: 17 (DXLVVPFDY); (d) an immunoglobulin light chain CDR1 (CDR-L1) comprising the amino acid sequence set forth in SEQ ID NO: 10 (SSDIGSNR); (e) an immunoglobulin light chain CDR2 (CDR-L2) comprising the amino acid sequence set forth in SEQ ID NO: 11 (SND); or (f) an immunoglobulin light chain CDR3 (CDR-L3) comprising the amino acid sequence set forth in SEQ ID NO: 12 (AAWDDSLSTYV); wherein X is any amino acid.

Described herein is a recombinant antibody or antigen binding fragment thereof that binds periostin, wherein the antibody or antigen binding fragment thereof comprises any one, two, three, four, or five complementarity determining regions selected from: (a) an immunoglobulin heavy chain CDR1 (CDR-H1) comprising the amino acid sequence set forth in SEQ ID NO: 1 (GYTFTSYG); (b) an immunoglobulin heavy chain CDR2 (CDR-H2) comprising an amino acid sequence set forth in SEQ ID NO: 16 (ISAYXGNT); (c) an immunoglobulin heavy chain CDR3 (CDR-H3) comprising an amino acid sequence set forth in SEQ ID NO: 17 (DXLVVPFDY); (d) an immunoglobulin light chain CDR1 (CDR-L1) comprising the amino acid sequence set forth in SEQ ID NO: 10 (SSDIGSNR); (e) an immunoglobulin light chain CDR2 (CDR-L2) comprising the amino acid sequence set forth in SEQ ID NO: 11 (SND); and (f) an immunoglobulin light chain CDR3 (CDR-L3) comprising the amino acid sequence set forth in SEQ ID NO: 12 (AAWDDSLSTYV); wherein X is any amino acid.

Described herein is a recombinant antibody or antigen binding fragment thereof that binds periostin, wherein the antibody or antigen binding fragment thereof comprises: (a) an immunoglobulin heavy chain CDR1 (CDR-H1) comprising the amino acid sequence set forth in SEQ ID NO: 1 (GYTFTSYG); (b) an immunoglobulin heavy chain CDR2 (CDR-H2) comprising an amino acid sequence set forth in any one of SEQ ID NOs: 2 (ISAYNGNT), 3 (ISAYSGNT), 4 (ISAYQGNT), 5 (ISAYTGNT), or 6 (ISAYDGNT); (c) an immunoglobulin heavy chain CDR3 (CDR-H3) comprising an amino acid sequence set forth in any one of SEQ ID NOs: 7 (DILVVPFDY), 8 (DVLVVPFDY), or 9 (DMLVVPFDY); (d) an immunoglobulin light chain CDR1 (CDR-L1) comprising the amino acid sequence set forth in SEQ ID NO: 10 (SSDIGSNR); (e) an immunoglobulin light chain CDR2 (CDR-L2) amino comprising the amino acid sequence set forth in SEQ ID NO: 11 (SND); (f) and an immunoglobulin light chain CDR3 (CDR-L3) comprising the amino acid sequence set forth in SEQ ID NO: 12 (AAWDDSLSTYV). In certain embodiments, the antibody is a human, humanized, or chimeric antibody. In certain embodiments, the antibody is an IgG antibody. In certain embodiments, the antibodies described herein can comprise an Fc portion with a lack of or reduced effector function. In certain embodiments, the antibody has an IC50 of less than about 50 nanomolar in a cell adhesion assay performed with human lung fibroblast cells and/or mouse fibroblast cells. In certain embodiments, the antibody has an IC50 of less than about 40 nanomolar in a cell adhesion assay performed with human lung fibroblast cells and/or mouse fibroblast cells. In certain embodiments, the antibody has an IC50 of less than about 30 nanomolar in a cell adhesion assay performed with human lung fibroblast cells and/or mouse fibroblast cells.

Also described herein is a recombinant antibody or antigen binding fragment wherein the antibody or antigen binding fragment thereof comprises: (a) an immunoglobulin heavy chain CDR1 (CDR-H1) comprising the amino acid sequence set forth in SEQ ID NO: 1 (GYTFTSYG); (b) an immunoglobulin heavy chain CDR2 (CDR-H2) comprising the amino acid sequence set forth in SEQ ID NO: 2 (ISAYNGNT); (c) an immunoglobulin heavy chain CDR3 (CDR-H3) comprising the amino acid sequence set forth in SEQ ID NO: 9 (DMLVVPFDY); (d) an immunoglobulin light chain CDR1 (CDR-L1) comprising the amino acid sequence set forth in SEQ ID NO: 10 (SSDIGSNR); (e) an immunoglobulin light chain CDR2 (CDR-L2) comprising the amino acid sequence set forth in SEQ ID NO: 11 (SND); and (f) an immunoglobulin light chain CDR3 (CDR-L3) comprising the amino acid sequence set forth in SEQ ID NO: 12 (AAWDDSLSTYV). In certain embodiments, the antibody is a human, humanized, or chimeric antibody. In certain embodiments, the antibody is an IgG antibody. In certain embodiments, the antibodies described herein can comprise an Fc portion with a lack of or reduced effector function. In certain embodiments, the antibody has an IC50 of less than about 50 nanomolar in a cell adhesion assay performed with human lung fibroblast cells and/or mouse fibroblast cells. In certain embodiments, the antibody has an IC50 of less than about 40 nanomolar in a cell adhesion assay performed with human lung fibroblast cells and/or mouse fibroblast cells. In certain embodiments, the antibody has an IC50 of less than about 30 nanomolar in a cell adhesion assay performed with human lung fibroblast cells and/or mouse fibroblast cells.

Also described herein is a recombinant antibody or antigen binding fragment thereof that binds periostin, comprising an immunoglobulin heavy chain and an immunoglobulin light chain: (a) wherein the immunoglobulin heavy chain comprises an amino acid sequence which is at least about 90%, 95%, 97%, 99%, or which is 100% identical to that set forth in SEQ ID NO: 13; and (b) wherein the immunoglobulin light chain comprises an amino acid sequence which is at least about 90%, 95%, 97%, 99%, or which is 100% identical to that set forth in SEQ ID NO: 14, wherein amino acid residue number 55 of SEQ ID NO 13: is asparagine, serine, glutamine, threonine, or aspartic acid, and wherein amino acid residue number 100 of SEQ ID NO: 13 is methionine, isoleucine, or valine. In certain embodiments, the antibody is an IgG antibody. In certain embodiments, the antibodies described herein can comprise an Fc portion with a lack of or reduced effector function. In certain embodiments, the antibody has an IC50 of less than about 50 nanomolar in a cell adhesion assay performed with human lung fibroblast cells and/or mouse fibroblast cells. In certain embodiments, the antibody has an IC50 of less than about 40 nanomolar in a cell adhesion assay performed with human lung fibroblast cells and/or mouse fibroblast cells. In certain embodiments, the antibody has an IC50 of less than about 30 nanomolar in a cell adhesion assay performed with human lung fibroblast cells and/or mouse fibroblast cells.

The antibody binding regions, including variable regions and CDR regions, described herein may suitably be formatted as part of an antibody with reduced effector function. In certain embodiments, the antibody may be a F(ab')2, which lacks the Fc region. In certain embodiments, the antibody may comprise one or more mutations to the constant region of an antibody heavy chain that reduces effector function, such as antibody dependent cellular cytotoxicity or complement dependent cytotoxicity. In certain embodiments, the antibody may comprise an IgG4 constant region. In certain embodiments, the one or more mutations to reduce one or more effector functions of the recombinant antibody or antigen binding fragment thereof comprise a mutation or set of mutations selected from: N434A, N434H, T307A/E380A/N434A, M252Y/S254T/T256E, 433K/434F/436H, T250Q, T250F, M428L, M428F, T250Q/M428L, N434S, V308W, V308Y, V308F, M252Y/M428L, D259I/V308F, M428L/V308F, Q311V/N434S, T307Q/N434A, E258F/V427T, S228P, L235E, S228P/L235E/R409K, S228P/L235E, K370Q, K370E, deletion of G446, deletion of K447, and any combination thereof of IgG4 according to the EU numbering system. In certain embodiments, the antibody may comprise an IgG4 constant region which has a mutation corresponding to S228P of the heavy chain according to the EU numbering system. In certain embodiments, the antibody may comprise an IgG4PAA constant region, which has mutations corresponding to S228P, F234A, and L235A of the heavy chain according to the EU numbering system. See Parekh et al. "Development and validation of an antibody-dependent cell-mediated cytotoxicity-reporter gene assay." MAbs 2012 May 1; 4(3): 310-318.

In some embodiments, the antibodies described herein exhibit decreased affinities to Clq relative to a corresponding wildtype antibody. In some embodiments, antibodies exhibit affinities for Clq receptor that are at least 2-fold, or at least 3-fold, or at least 5-fold, or at least 7-fold, or at least 10-fold, or at least 20-fold, or at least 30-fold, or at least 40-fold, or at least 50-fold, or at least 60-fold, or at least 70-fold, or at least 80-fold, or at least 90-fold, or at least 100-fold, or at least 200-fold less than the corresponding wildtype antibody.

In some embodiments, the antibodies described herein exhibit affinities for Clq that are at least 90%, at least 80%, at least 70%, at least 60%, at least 50%, at least 40%, at least 30%, at least 20%, at least 10%, or at least 5% less than that of the corresponding wildtype antibody. In some embodiments, the antibodies described herein exhibit affinities for Clq that are between about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In some embodiments, the antibodies described herein exhibit affinities for Clq that are greater than 1 μM, greater than 5 μM, greater than 10 μM, greater than 25 μM, greater than 50 μM, or greater than 100 μM.

In some embodiments, the antibodies described herein exhibit decreased CDC activities as compared to the corresponding wildtype Fc antibody. In some embodiments, the antibodies described herein exhibit CDC activities that are at least 2-fold, or at least 3-fold, at least 4-fold, at least 5-fold, at least 10-fold, at least 50-fold, or at least 100-fold less than that of the corresponding wildtype antibody. In some embodiments, the antibodies described herein exhibit CDC activities that are reduced by at least 10%, or at least 20%, or by at least 30%), or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to the corresponding wildtype antibody. In some embodiments, the antibodies described herein exhibit no detectable CDC activities. In some embodiments, the reduction and/or ablation of CDC activity may be attributed to the reduced affinity of the antibodies described herein for Fc ligands and/or receptors.

It is understood in the art that biological therapies may have adverse toxicity issues associated with the complex nature of directing the immune system to recognize and attack unwanted cells and/or targets. When the recognition and/or the targeting for attack do not take place where the treatment is required, consequences such as adverse toxicity may occur. For example, antibody staining of non-targeted tissues may be indicative of potential toxicity issues. In some embodiments, the antibodies described herein exhibit reduced staining of non-targeted tissues as compared to the corresponding wildtype antibody. In some embodiments, the antibodies described herein exhibit reduced staining of non-targeted tissues that are at least 2-fold, or at least 3-fold, or at least 5-fold, or at least 7-fold, or at least 10-fold, or at least 20-fold, or at least 30-fold, or at least 40-fold, or at least 50-fold, or at least 60-fold, or at least 70-fold, or at least 80-fold, or at least 90-fold, or at least 100-fold, or at least 200-fold less than that of to the corresponding wildtype antibody. In some embodiments, the antibodies described herein exhibit reduced staining of non-targeted tissues that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to the corresponding wildtype antibody.

In some embodiments, the antibodies described herein exhibit a reduced antibody related toxicity as compared to the corresponding wildtype antibody. In some embodiments, the antibodies described herein exhibit toxicities that are at least 2-fold, or at least 3-fold, or at least 5-fold, or at least 7-fold, or at least 10-fold, or at least 20-fold, or at least 30-fold, or at least 40-fold, or at least 50-fold, or at least 60-fold, or at least 70-fold, or at least 80-fold, or at least 90-fold, or at least 100-fold, or at least 200-fold less than that of the corresponding wildtype antibody. In some embodiments, the antibodies described herein exhibit toxicities that are reduced by at least 10%, or at least 20%, or by at least 30%, or by at least 40%, or by at least 50%, or by at least 60%, or by at least 70%), or by at least 80%, or by at least 90%, or by at least 100%, or by at least 200%, or by at least 300%, or by at least 400%, or by at least 500% relative to the corresponding wildtype antibody.

It is understood in the art that biological therapies may have as adverse effect thrombocyte aggregation. In vitro and in vivo assays could be used for measuring thrombocyte aggregation. In some embodiments, the antibodies described herein exhibit reduced thrombocyte aggregation in an in vitro assay compared to the corresponding wildtype antibody. In some embodiments, the antibodies described herein exhibit reduced thrombocyte aggregation in an in vitro assay that is at least 2-fold, or at least 3-fold, or at least 5-fold, or at least 7-fold, or at least 10-fold, or at least 20-fold, or at least 30-fold, or at least 40-fold, or at least 50-fold, or at least 60-fold, or at least 70-fold, or at least 80-fold, or at least 90-fold, or at least 100-fold, or at least 200-fold less than that of the corresponding wildtype antibody. In some embodiments, the antibodies described herein exhibit reduced thrombocyte aggregation in an in vitro assay that is reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to the corresponding wildtype antibody.

In some embodiments, the antibodies described herein exhibit a reduced in vivo thrombocyte aggregation compared to the corresponding wildtype antibody. In some embodiments, the antibodies described herein exhibit reduced thrombocyte aggregation in an in vivo assay that is at least 2-fold, or at least 3-fold, or at least 5-fold, or at least 7-fold, or at least 10-fold, or at least 20-fold, or at least 30-fold, or at least 40-fold, or at least 50-fold, or at least 60-fold, or at least 70-fold, or at least 80-fold, or at least 90-fold, or at least 100-fold, or at least 200-fold less than that of the corresponding wildtype antibody. In some embodiments, the antibodies described herein exhibit reduced thrombocyte aggregation in an in vivo assay that is reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to the corresponding wildtype antibody.

In some embodiments, the antibodies described herein exhibit reduced platelet activation and/or platelet aggregation as compared to the corresponding wildtype antibody.

Epitopes Bound by Therapeutically Useful Periostin Antibodies

Described herein is a unique epitope or region of human periostin that when bound inhibits periostin biological activity (e.g., integrin mediated cell attachment) and alters the tumor microenvironment (collagen remodeling and changes in immune cells). This binding is a combination of weak (Van der Waals attraction), medium (hydrogen binding), and strong (salt bridge) interactions between an antibody CDR amino acid residue and amino acid residues in periostin (e.g., contact residues). In certain embodiments, a contact residue is a residue on periostin that forms a hydrogen bond with a residue on an anti-periostin antibody. In certain embodiments, a contact residue is a residue on periostin that forms a salt bridge with a residue on an anti-periostin antibody. In certain embodiments, a contact residue is a residue on periostin that results in a Van der Waals attraction with and is within at least 5, 4, or 3 angstroms of a residue on an anti-periostin antibody.

In certain embodiments, the anti-periostin antibodies described herein do not bind to Tenascin C or collagen, Type I.

In certain embodiments, described herein is an isolated antibody that binds any one, two, three, four, five, or six of the following residues: N276, R284, E288, L287, V295, or K302 of periostin (SEQ ID NO: 15). In certain embodiments, described herein is an isolated antibody that binds all of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that participate with the antibody in strong interactions. In some embodiments, the antibody increases interferon gamma expression and/or release by CD8+ T cells in tumor sites. In some embodiments, the antibody reduces accumulation of suppressive granulocytic myeloid cells and/or TAMs tumor associated macrophages in infiltrating tumors. In some embodiments, the antibody increases the pro-inflammatory M1 macrophage phenotype and/or reduces the M2 macrophage phenotype in infiltrating tumors. In some embodiments, the antibody increases CD8+ T cells to tumor sites, decreases TAMs, and increases the pro-inflammatory M1 macrophage phenotype in infiltrating tumors.

In certain embodiments, described herein is an antibody comprising CDRs with an amino acid sequence set forth in any one of SEQ ID NOs: 1, 2, 3, 4, 5, 6, 7, 8, 9, 10, 11, and 12 that binds any one, two, three, four, five, or six, of the following residues: N276, R284, E288, L287, V295, or K302 of SEQ ID NO: 15. In certain embodiments, described herein is an antibody comprising CDRs with an amino acid sequence set forth in any one of SEQ ID NOs: 1, 2, 3, 4, 5, 6, 7, 8, 9, 10, 11, and 12 that binds to all of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that participate with the antibody in strong interactions.

In certain embodiments, described herein is an antibody comprising CDRs that differ from the amino acid sequence set forth in any one of SEQ ID NOs: 1, 2, 3, 4, 5, 6, 7, 8, 9, 10, 11, and 12 that binds any one, two, three, four, five, or six, of the following residues: N276, R284, E288, L287, V295, or K302 of SEQ ID NO: 15. In certain embodiments, described herein is an antibody comprising CDRs that differ from the amino acid sequence set forth in any one of SEQ ID NOs: 11, 2, 3, 4, 5, 6, 7, 8, 9, 10, 11, and 12 that binds any one, two, three, four, five, or six, of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that participate with the antibody in strong interactions.

In certain embodiments, described herein is an antibody comprising CDRs that differ by 1, 2, 3, 4, or 5 amino acid residues from the amino acid sequence set forth in any one of SEQ ID NOs: 1, 2, 3, 4, 5, 6, 7, 8, 9, 10, 11, and 12, and that binds any one, two, three, four, five, or six, of the following residues: N276, R284, E288, L287, V295, or K302 of SEQ ID NO: 15. In certain embodiments, described herein is an antibody comprising CDRs that differ from the amino acid sequence set forth in any one of SEQ ID NOs: 1, 2, 3, 4, 5, 6, 7, 8, 9, 10, 11, and 12 that binds any one, two, three, four, five, or six, of the following residues: N276, R284, E288, L287, V295, or K302 of SEQ ID NO: 15. In certain embodiments, the antibody only binds residues that that participate with the antibody in strong or medium interactions. In certain embodiments, the antibody only binds residues that that participate with the antibody in strong interactions.

In certain embodiments, described herein, is an antibody that specifically binds periostin comprising a human or humanized heavy chain variable region amino acid sequence at least about 80%, about 90%, about 95%, about 97%, about 98%, or about 99% identical to the amino acid sequence set forth in SEQ ID NO:13; and a human or humanized light chain variable region amino acid sequence at least about 80%, about 90%, about 95%, about 97%, about 98%, or about 99% identical to the amino acid sequence set forth in SEQ ID NO: 14 and binds one, two, three, four, five, or six, of the following residues: N276, R284, E288, L287, V295, or K302 of SEQ ID NO: 15. In certain embodiments, described herein, is an antibody that specifically binds periostin comprising a human or humanized heavy chain variable region amino acid sequence at least about 80%, about 90%, about 95%, about 97%, about 98%, or about 99% identical to the amino acid sequence set forth in SEQ ID NO: 13; and a human or humanized light chain variable region amino acid sequence at least about 80%, about 90%, about 95%, about 97%, about 98%, or about 99% identical to the amino acid sequence set forth in SEQ ID NO: 14 and binds all of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that that participate with the antibody in strong interactions.

In certain embodiments, described herein is an antibody comprising CDRs with an amino acid sequence set forth in any one of SEQ ID NOs: 1, 2, 3, 4, 5, 6, 7, 8, 9, 10, 11, and 12 and comprises a human or humanized heavy chain variable region amino acid sequence at least about 80%, about 90%, about 95%, about 97%, about 98%, or about 99% identical to the amino acid sequence set forth in SEQ ID NO:13; and a human or humanized light chain variable region amino acid sequence at least about 80%, about 90%, about 95%, about 97%, about 98%, or about 99% identical to the amino acid sequence set forth in SEQ ID NO: 14 and binds any one, two, three, four, five, or six, of the following residues: N276, R284, E288, L287, V295, or K302 of SEQ ID NO: 15. In certain embodiments, described herein is an antibody comprising CDRs with an amino acid sequence set forth in any one of SEQ ID NOs: 1, 2, 3, 4, 5, 6, 7, 8, 9, 10, 11, and 12 that binds to all of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that participate with the antibody in strong interactions.

In certain embodiments, described herein, is an antibody that specifically binds periostin comprising a human or humanized heavy chain variable region amino acid sequence at least about 80%, about 90%, about 95%, about 97%, about 98%, or about 99% identical to the amino acid sequence set forth in SEQ ID NO:13 wherein amino acid residue number 55 of SEQ ID NO: 13 is asparagine, serine, glutamine, threonine, or aspartic acid, and wherein amino acid residue number 100 of SEQ ID NO: 13 is methionine, isoleucine, or valine; and a human or humanized light chain variable region amino acid sequence at least about 80%, about 90%, about 95%, about 97%, about 98%, or about 99% identical to the amino acid sequence set forth in SEQ ID NO: 14 and binds one, two, three, four, five, or six, of the following residues: N276, R284, E288, L287, V295, or K302 of SEQ ID NO: 15. In certain embodiments, described herein, is an antibody that specifically binds periostin comprising a human or humanized heavy chain variable region amino acid sequence at least about 80%, about 90%, about 95%, about 97%, about 98%, or about 99% identical to the amino acid sequence set forth in SEQ ID NO: 13 wherein amino acid residue number 55 of SEQ ID NO: 13 is asparagine, serine, glutamine, threonine, or aspartic acid, and wherein amino acid residue number 100 of SEQ ID NO: 13 is methionine, isoleucine, or valine; and a human or humanized light chain variable region amino acid sequence at least about 80%, about 90%, about 95%, about 97%, about 98%, or about 99% identical to the amino acid sequence set forth in SEQ ID NO: 14 and binds all of the following residues: N276, R284, E288, L287, V295, or K302 of SEQ ID NO: 15. In certain embodiments, the antibody only binds residues that that participate with the antibody in strong or medium interactions. In certain embodiments, the antibody only binds residues that that participate with the antibody in strong interactions.

In certain embodiments, described herein, is an antibody that specifically binds periostin comprising CDRs with an amino acid sequence set forth in any one of SEQ ID NOs: 1, 2, 3, 4, 5, 6, 7, 8, 9, 10, 11, and 12 and a human or humanized heavy chain variable region amino acid sequence at least about 80%, about 90%, about 95%, about 97%, about 98%, or about 99% identical to the amino acid sequence set forth in SEQ ID NO:13 wherein amino acid residue number 55 of SEQ ID NO: 13 is asparagine, serine, glutamine, threonine, or aspartic acid, and wherein amino acid residue number 100 of SEQ ID NO: 13 is methionine, isoleucine, or valine; and a human or humanized light chain variable region amino acid sequence at least about 80%, about 90%, about 95%, about 97%, about 98%, or about 99% identical to the amino acid sequence set forth in SEQ ID NO: 14 and binds one, two, three, four, five, or six, of the following residues: N276, R284, E288, L287, V295, or K302 of SEQ ID NO: 15. In certain embodiments, described herein, is an antibody that specifically binds periostin comprising CDRs with an amino acid sequence set forth in any one of SEQ ID NOs: 1, 2, 3, 4, 5, 6, 7, 8, 9, 10, 11, and 12 and a human or humanized heavy chain variable region amino acid sequence at least about 80%, about 90%, about 95%, about 97%, about 98%, or about 99% identical to the amino acid sequence set forth in SEQ ID NO: 13 wherein amino acid residue number 55 of SEQ ID NO: 13 is asparagine, serine, glutamine, threonine, or aspartic acid, and wherein amino acid residue number 100 of SEQ ID NO: 13 is methionine, isoleucine, or valine; and a human or humanized light chain variable region amino acid sequence at least about 80%, about 90%, about 95%, about 97%, about 98%, or about 99% identical to the amino acid sequence set forth in SEQ ID NO: 14 and binds all of the following residues: N276, R284, E288, L287, V295, or K302 of SEQ ID NO: 15. In certain embodiments, the antibody only binds residues that that participate with the antibody in strong or medium interactions. In certain embodiments, the antibody only binds residues that that participate with the antibody in strong interactions.

In certain embodiments, described herein is an antibody that competes for binding with an antibody comprising CDRs with an amino acid sequence set forth in any one of SEQ ID NOs: 1, 2, 3, 4, 5, 6, 7, 8, 9, 10, 11, and 12 and binds any one, two, three, four, five, or six, of the following residues: N276, R284, E288, L287, V295, or K302 of SEQ ID NO: 15. In certain embodiments, described herein is an antibody that competes with binding with an antibody comprising CDRs with an amino acid sequence set forth in any one of SEQ ID NOs: 1, 2, 3, 4, 5, 6, 7, 8, 9, 10, 11, and 12 that binds to all of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that participate with the antibody in strong interactions.

In certain embodiments, described herein is an antibody comprising a binding region that at least partially overlaps with the binding region of an antibody comprising CDRs with an amino acid sequence set forth in any one of SEQ ID NOs: 1, 2, 3, 4, 5, 6, 7, 8, 9, 10, 11, and 12 and binds any one, two, three, four, five, or six, of the following residues: N276, R284, E288, L287, V295, or K302 of SEQ ID NO: 15. In certain embodiments, described herein is an antibody comprising a binding region that at least partially overlaps with the binding region of an antibody comprising CDRs with an amino acid sequence set forth in any one of SEQ ID NOs: 1, 2, 3, 4, 5, 6, 7, 8, 9, 10, 11, and 12 that binds to all of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that participate with the antibody in strong interactions.

In certain embodiments, described herein is an antibody that competes for binding with an antibody comprising a human or humanized heavy chain variable region amino acid sequence at least about 80%, about 90%, about 95%, about 97%, about 98%, or about 99% identical to the amino acid sequence set forth in SEQ ID NO:13; and a human or humanized light chain variable region amino acid sequence at least about 80%, about 90%, about 95%, about 97%, about 98%, or about 99% identical to the amino acid sequence set forth in SEQ ID NO: 14.

In certain embodiments, described herein is an antibody comprising a binding region that at least partially overlaps with the binding region of an antibody comprising a human or humanized heavy chain variable region amino acid sequence at least about 80%, about 90%, about 95%, about 97%, about 98%, or about 99% identical to the amino acid sequence set forth in SEQ ID NO:13; and a human or humanized light chain variable region amino acid sequence at least about 80%, about 90%, about 95%, about 97%, about 98%, or about 99% identical to the amino acid sequence set forth in SEQ ID NO: 14.

In certain embodiments, described herein is an antibody that competes for binding with an antibody comprising CDRs with an amino acid sequence set forth in any one of SEQ ID NOs: 1, 2, 3, 4, 5, 6, 7, 8, 9, 10, 11, and 12 and comprises a human or humanized heavy chain variable region amino acid sequence at least about 80%, about 90%, about 95%, about 97%, about 98%, or about 99% identical to the amino acid sequence set forth in SEQ ID NO:13; and a human or humanized light chain variable region amino acid sequence at least about 80%, about 90%, about 95%, about 97%, about 98%, or about 99% identical to the amino acid sequence set forth in SEQ ID NO: 14 and binds any one, two, three, four, five, or six, of the following residues: N276, R284, E288, L287, V295, or K302 of SEQ ID NO: 15. In certain embodiments, described herein is an antibody comprising CDRs with an amino acid sequence set forth in any one of SEQ ID NOs: 1, 2, 3, 4, 5, 6, 7, 8, 9, 10, 11, and 12 that binds to all of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that participate with the antibody in strong interactions.

In certain embodiments, described herein is an antibody comprising a binding region that at least partially overlaps with the binding region of an antibody comprising CDRs with an amino acid sequence set forth in any one of SEQ ID NOs: 1, 2, 3, 4, 5, 6, 7, 8, 9, 10, 11, and 12 and comprises a human or humanized heavy chain variable region amino acid sequence at least about 80%, about 90%, about 95%, about 97%, about 98%, or about 99% identical to the amino acid sequence set forth in SEQ ID NO:13; and a human or humanized light chain variable region amino acid sequence at least about 80%, about 90%, about 95%, about 97%, about 98%, or about 99% identical to the amino acid sequence set forth in SEQ ID NO: 14 and binds any one, two, three, four, five, or six, of the following residues: N276, R284, E288, L287, V295, or K302 of SEQ ID NO: 15. In certain embodiments, described herein is an antibody comprising CDRs with an amino acid sequence set forth in any one of SEQ ID NOs: 1, 2, 3, 4, 5, 6, 7, 8, 9, 10, 11, and 12 that binds to all of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that participate with the antibody in strong interactions.

In certain embodiments, described herein is an antibody that competes for binding with an antibody comprising CDRs with an amino acid sequence set forth in any one of SEQ ID NOs: 1, 2, 3, 4, 5, 6, 7, 8, 9, 10, 11, and 12 and comprises a human or humanized heavy chain variable region amino acid sequence at least about 80%, about 90%, about 95%, about 97%, about 98%, or about 99% identical to the amino acid sequence set forth in SEQ ID NO:13 wherein amino acid residue number 55 of SEQ ID NO: 13 is asparagine, serine, glutamine, threonine, or aspartic acid, and wherein amino acid residue number 100 of SEQ ID NO: 13 is methionine, isoleucine, or valine; and a human or humanized light chain variable region amino acid sequence at least about 80%, about 90%, about 95%, about 97%, about 98%, or about 99% identical to the amino acid sequence set forth in SEQ ID NO: 14 and binds any one, two, three, four, five, or six, of the following residues: N276, R284, E288, L287, V295, or K302 of SEQ ID NO: 15. In certain embodiments, described herein is an antibody comprising CDRs with an amino acid sequence set forth in any one of SEQ ID NOs: 1, 2, 3, 4, 5, 6, 7, 8, 9, 10, 11, and 12 that binds to all of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that participate with the antibody in strong interactions.

In certain embodiments, described herein is an antibody comprising a binding region that at least partially overlaps with the binding region of an antibody comprising CDRs with an amino acid sequence set forth in any one of SEQ ID NOs: 1, 2, 3, 4, 5, 6, 7, 8, 9, 10, 11, and 12 and comprises a human or humanized heavy chain variable region amino acid sequence at least about 80%, about 90%, about 95%, about 97%, about 98%, or about 99% identical to the amino acid sequence set forth in SEQ ID NO:13 wherein amino acid at residue number 55 of SEQ ID NO: 13 is asparagine, serine, glutamine, threonine, or aspartic acid, and wherein the amino acid at residue 100 of SEQ ID NO: 13 is methionine, isoleucine, or valine; and a human or humanized light chain variable region amino acid sequence at least about 80%, about 90%, about 95%, about 97%, about 98%, or about 99% identical to the amino acid sequence set forth in SEQ ID NO: 14 and binds any one, two, three, four, five, or six, of the following residues: N276, R284, E288, L287, V295, or K302 of SEQ ID NO: 15. In certain embodiments, described herein is an antibody comprising CDRs with an amino acid sequence set forth in any one of SEQ ID NOs: 1, 2, 3, 4, 5, 6, 7, 8, 9, 10, 11, and 12 that binds to all of the following residues: N276, R284, E288, L287, V295, or K302 of SEQ ID NO: 15. In certain embodiments, the antibody only binds residues that participate with the antibody in strong or medium interactions. In certain embodiments, the antibody only binds residues that participate with the antibody in strong interactions.

Therapeutic Methods

The antibodies disclosed herein are antibodies useful for the treatment of a cancer or tumor. Treatment refers to a method that seeks to improve or ameliorate the condition being treated. With respect to cancer treatment includes, but is not limited to, reduction of tumor volume, reduction in growth of tumor volume, increase in progression-free survival, or overall life expectancy. In certain embodiments, treatment will affect remission of a cancer being treated. In certain embodiments, treatment encompasses use as a prophylactic or maintenance dose intended to prevent reoccurrence or progression of a previously treated cancer or tumor. It is understood by those of skill in the art that while an antibody may be safe and effective, not all individuals will respond equally to a treatment that is administered, nevertheless these individuals are considered to be treated.

Tumors treatable by the antibodies described herein include those that express periostin. Periostin is a component of the extracellular matrix, which is secreted by cancer associated fibroblasts, and, as such, most tumors will express or comprise periostin. In certain embodiments, the tumor treated is one that is periostin positive and has detectable periostin or is known to have detectible periostin based upon a population analysis of like tumors. In certain embodiments, a periostin high tumor is one that has an IHC-score of about 50 or more.

In certain embodiments, the cancer or tumor is a solid cancer or tumor. In certain embodiments, the cancer or tumor is a blood cancer or tumor. In certain embodiments, the cancer or tumor comprises breast, heart, lung, small intestine, colon, spleen, kidney, bladder, head, neck, ovarian, prostate, brain, pancreatic, skin, bone, bone marrow, blood, thymus, uterine, testicular, or liver tumors. In certain embodiments, tumors or cancers which can be treated with the antibodies of the invention comprise adenoma, adenocarcinoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and/or teratoma. In certain embodiments, the tumor/cancer is selected from the group of acral lentiginous melanoma, actinic keratosis, adenocarcinoma, adenoid cystic carcinoma, adenomas, adenosarcoma, adenosquamous carcinoma, astrocytic tumors, Bartholin gland carcinoma, basal cell carcinoma, bronchial gland carcinoma, capillary carcinoid, carcinoma, carcinosarcoma, cholangiocarcinoma, chondrosarcoma, cystadenoma, endodermal sinus tumor, endometrial hyperplasia, endometrial stromal sarcoma, endometrioid adenocarcinoma, ependymal sarcoma, Swing's sarcoma, focal nodular hyperplasia, gastronoma, germ line tumors, glioblastoma, glucagonoma, hemangioblastoma, hemangioendothelioma, hemangioma, hepatic adenoma, hepatic adenomatosis, hepatocellular carcinoma, insulinite, intraepithelial neoplasia, intraepithelial squamous cell neoplasia, invasive squamous cell carcinoma, large cell carcinoma, liposarcoma, lung carcinoma, lymphoblastic leukemia, lymphocytic leukemia, leiomyosarcoma, melanoma, malignant melanoma, malignant mesothelial tumor, nerve sheath tumor, medulloblastoma, medulloepithelioma, mesothelioma, mucoepidermoid carcinoma, myeloid leukemia, neuroblastoma, neuroepithelial adenocarcinoma, nodular melanoma, osteosarcoma, ovarian carcinoma, papillary serous adenocarcinoma, pituitary tumors, plasmacytoma, pseudosarcoma, prostate carcinoma, pulmonary blastoma, renal cell carcinoma, retinoblastoma, rhabdomyosarcoma, sarcoma, serous carcinoma, squamous cell carcinoma, small cell carcinoma, soft tissue carcinoma, somatostatin secreting tumor, squamous carcinoma, squamous cell carcinoma, undifferentiated carcinoma, uveal melanoma, verrucous carcinoma, vagina/vulva carcinoma, VIPoma, and Wilm's tumor. In certain embodiments, the tumor/cancer to be treated with one or more antibodies of the invention comprise brain cancer, head and neck cancer, head and neck squamous cell carcinoma, colorectal carcinoma, acute myeloid leukemia, pre-B-cell acute lymphoblastic leukemia, bladder cancer, astrocytoma, preferably grade II, III or IV astrocytoma, glioblastoma, glioblastoma multiforme, small cell cancer, and non-small cell cancer, preferably non-small cell lung cancer, lung adenocarcinoma, metastatic melanoma, androgen-independent metastatic prostate cancer, androgen-dependent metastatic prostate cancer, prostate adenocarcinoma, and breast cancer, preferably breast ductal cancer, and/or breast carcinoma. In some embodiments, the cancer comprises glioblastoma, pancreatic cancer, breast cancer, bladder cancer, kidney cancer, head and neck cancer, ovarian cancer, skin cancer, stomach cancer, mesothelioma, liver cancer, endometrial cancer, colon cancer, cervical cancer, prostate cancer, or lung cancer. In certain embodiments, the cancer treated with the antibodies of this disclosure comprises glioblastoma. In certain embodiments, the cancer treated with one or more antibodies of this disclosure comprises pancreatic cancer. In certain embodiments, the cancer treated with one or more antibodies of this disclosure comprises ovarian cancer. In certain embodiments, the cancer treated with one or more antibodies of this disclosure comprises lung cancer. In certain embodiments, the cancer treated with one or more antibodies of this disclosure comprises squamous cell lung cancer. In certain embodiments, the cancer treated with one or more antibodies of this disclosure comprises prostate cancer. In certain embodiments, the cancer treated with one or more antibodies of this disclosure comprises colon cancer. In certain embodiments, the cancer treated comprises glioblastoma, pancreatic cancer, ovarian cancer, colon cancer, prostate cancer, or lung cancer. In a certain embodiment, the cancer is refractory to other treatment. In a certain embodiment, the cancer treated is relapsed. In a certain embodiment, the cancer is a relapsed/refractory glioblastoma, pancreatic cancer, ovarian cancer, colon cancer, prostate cancer, or lung cancer.

In certain embodiments, the antibodies can be administered to a subject in need thereof by any route suitable for the administration of antibody-containing pharmaceutical compositions, such as, for example, subcutaneous, intraperitoneal, intravenous, intramuscular, intratumoral, or intracerebral, etc. In certain embodiments, the antibodies are administered intravenously. In certain embodiments, the antibodies are administered subcutaneously. In certain embodiments, the antibodies are administered intratumoral. In certain embodiments, the antibodies are administered on a suitable dosage schedule, for example, weekly, twice weekly, monthly, twice monthly, once every two weeks, once every three weeks, or once a month etc. In certain embodiments, the antibodies are administered once every three weeks. The antibodies can be administered in any therapeutically effective amount. In certain embodiments, the therapeutically acceptable amount is between about 0.1 mg/kg and about 50 mg/kg. In certain embodiments, the therapeutically acceptable amount is between about 1 mg/kg and about 40 mg/kg. In certain embodiments, the therapeutically acceptable amount is between about 5 mg/kg and about 30 mg/kg. Therapeutically effective amounts include amounts are those sufficient to ameliorate one or more symptoms associated with the disease or affliction to be treated.

The anti-periostin antibodies described herein are also useful in a method of decreasing collagen content in a tumor in an individual.

The anti-periostin antibodies described herein are also useful in a method of increasing M1 macrophage phenotype and/or reducing M2 macrophage phenotype in a tumor in an individual.

The anti-periostin antibodies described herein are also useful in a method of reducing accumulation of suppressive granulocytic myeloid cells and/or tumor associated macrophages in an individual.

The anti-periostin antibodies described herein are also useful in a method of increasing the frequency of CD4+ and/or CD8+ T cells in a tumor of an individual.

The anti-periostin antibodies described herein are also useful in a method of increasing interferon gamma expression and/or release by CD8+ T cells in a tumor in an individual.

The antibodies described herein are useful in the manufacture of a medicament for decreasing collagen content in a tumor in an individual.

The antibodies described herein are useful in the manufacture of a medicament for increasing M1 macrophage phenotype and/or reducing M2 macrophage phenotype in a tumor in an individual.

The antibodies described herein are useful in the manufacture of a medicament for reducing accumulation of suppressive granulocytic myeloid cells and/or tumor associated macrophages in an individual.

The antibodies described herein are useful in the manufacture of a medicament for increasing the frequency of CD4+ and/or CD8+ T cells in a tumor of an individual.

The antibodies described herein are useful in the manufacture of a medicament for increasing interferon gamma expression and/or release by CD8+ T cells in a tumor in an individual.

Pharmaceutically Acceptable Excipients, Carriers, and Diluents

The antibodies described herein can be provided in isolated and purified form sufficiently pure for administration to a human individual.

In certain embodiments, the anti-periostin antibodies of the current disclosure are included in a pharmaceutical composition comprising one or more pharmaceutically acceptable excipients, carriers, and diluents. In certain embodiments, the antibodies of the current disclosure are administered suspended in a sterile solution. In certain embodiments, the solution comprises 0.9% NaCl, or 5% dextrose, glucose or sucrose. In certain embodiments, the solution further comprises one or more of: buffers, for example, acetate, citrate, histidine, succinate, phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA.

In certain embodiments, the antibodies of the current disclosure are shipped/stored lyophilized and reconstituted before administration. In certain embodiments, lyophilized antibody formulations comprise a bulking agent such as, mannitol, sorbitol, sucrose, trehalose, dextran 40, or combinations thereof. The lyophilized formulation can be contained in a vial comprised of glass or other suitable non-reactive material. The antibodies when formulated, whether reconstituted or not, can be buffered at a certain pH, generally less than 7.0. In certain embodiments, the pH can be between 4.5 and 6.5, 4.5 and 6.0, 4.5 and 5.5, 4.5 and 5.0, or 5.0 and 6.0.

Also described herein are kits comprising one or more of the antibodies described herein in a suitable container and one or more additional component selected from: instructions for use; a diluent, an excipient, a carrier, and a device for administration.

In certain embodiments, described herein is a method of preparing a cancer treatment comprising admixing one or more pharmaceutically acceptable excipients, carriers, or diluents and an antibody of the current disclosure. In certain embodiments, described herein is a method of preparing a cancer treatment for storage or shipping comprising lyophilizing one or more antibodies of the current disclosure.

Examples

The following illustrative examples are representative of embodiments of compositions and methods described herein and are not meant to be limiting in any way.

Example 1—Antibody Generation and Screening

A phage display antibody discovery campaign was performed to isolate binders against periostin using a fully human phage library. Briefly, three rounds of panning were conducted using either recombinant human periostin, recombinant mouse periostin, or combinations thereof, with an emphasis on identifying mouse cross-reactive binders. From this panning strategy, 78 sequence unique ScFv's that cross-react to mouse periostin were identified and produced in a human IgG1 format for functional screening in a cell attachment assay. See FIG. 1.

Recombinant human or mouse periostin was coated on 96 well plates overnight at 4° C. The next day, plates were washed with PBS and blocked with 2% BSA for 1 hour at 37° C. After blocking, antibodies were added to the plates and incubated for 30 min at 37° C. Following incubation, 50,000 IMR90 human lung fibroblast cells or 50,000 MLG mouse fibroblast cells were then added to the wells and allowed to incubate for 2 hr at 37° C. Plates were then washed twice with PBS and the confluency of the wells was measured using the IncuCyte platform. From a high concentration single dose screen at 500 nM, 21 IgGs were identified as having >50% inhibition as shown in FIG. 1, and were carried forward to binding screens to determine relative affinities to human and mouse periostin, as shown in Table 1 below.

To determine relative affinities for recombinant human or mouse periostin, these proteins were coated on maxisorp plates overnight at 4° C. The next day, plates were blocked with casein blocking buffer for 1 hr at 37° C. Titrations of each antibody were added to the plates and allowed to bind for 1 hr at RT. Plates were washed 4× with PBST followed by incubation with an HRP conjugated anti-human Fc secondary for 30 min at RT. Plates were then washed again with 4×PBST and then developed using TMB substrate and 1M HCl. From this screen, 4 clones were selected (Table 1 marked by bold and italics) that have <1 nM binding EC50 values to both human and mouse periostin.

TABLE 1

Binding EC50 values to human and mouse periostin for the 21 IgGs identified in the single point cell attachment assay shown in FIG. 1.

| EC50 (nM) | ***Nb0625*** | ***Nb0627*** | NB0629 | ***Nb0639*** | NB0640 | NB0765 | NB0776 |
|---|---|---|---|---|---|---|---|
| HuPOSTN | ***1.03*** | ***0.07*** | 0.09 | ***0.10*** | 9.30 | 1.08 | 36.60 |
| MoPOSTN | ***0.14*** | ***0.11*** | 6.08 | ***0.12*** | 6.41 | 2.41 | n.s. |
| EC50 (nM) | NB0784 | NB0791 | NB0792 | ***Nb0794*** | NB0798 | NB0800 | NB0801 |
| HuPOSTN | 4.68 | n.s. | 59.43 | ***0.08*** | 0.48 | n.s. | 25.16 |
| MoPOSTN | 32.76 | n.s. | 158.50 | ***0.35*** | 62.02 | n.s. | 22.36 |
| EC50 (nM) | NB0802 | NB0803 | NB0804 | NB0805 | NB0806 | NB0815 | NB0816 |
| HuPOSTN | 18.75 | 19.30 | n.s. | n.s. | n.s. | 1.05 | 1.00 |
| MoPOSTN | 25.02 | 27.44 | n.s. | n.s. | n.s. | 55.79 | n.s. |

Note
that n.s. denotes that no saturation was observed in the assay.

Example 2—Generation of NB0828 and Sequence Variants

The 4 candidates were retested in a dose response in the cell attachment assay to determine IC50 values. From this screen, NB0627 was identified as a particularly suitable IgG (Table 2).

TABLE 2

IC50 values for the top 4 cross-reactive binders/blockers identified in Table 1.

| IC50 (nM) | NB0625 | NB0627 | NB0639 | NB0794 |
|---|---|---|---|---|
| HuPOSTN | 243.3 | 22.4 | 236.8 | 73.1 |

NB0627 was then converted to an effector silent IgG4PAA isotype, generating lead candidate NB0828. Sequence analysis of NB0828 identified two post translational modification liabilities in the VH region. The first, a deamidation site, is located in the CDR-H2, and the second, an oxidation site, is located in the CDR-H3. Therefore, in an attempt to remove these liabilities, several single and double mutants were generated, and their binding and activity was measured. A summary of results for the IC50 and EC50 values for NB0828 and its variants are listed in Table 3.

TABLE 3

Binding and functional data summary of NB0828 and NB0828 variants.

| Assay | POSTN Form | NB0828 | NB1003 (N55S) | NB1010 (N55Q) | NB1011 (N55T) |
|---|---|---|---|---|---|
| CAA IC50 | Human | 24.34 | 10.75 | 7.97 | 15.03 |
| (nM) | Mouse | 25.97 | 14.91 | 19.60 | 22.31 |
| Binding | Human | 0.12 | 0.08 | 0.08 | 0.07 |
| EC50 | Mouse | 0.15 | 0.08 | 0.10 | 0.07 |
| (nM) | | | | | |
| Assay | POSTN Form | NB1015 (N55D) | NB1012 (N55S_ M100I) | NB1014 (N55T_ M10OV) | |
| CAA IC50 | Human | 13.63 | n.s. | n.s. | |
| (nM) | Mouse | 20.91 | 42.34 | 65.08 | |
| Binding | Human | 0.12 | 2.28 | 9.47 | |
| EC50 | Mouse | 0.18 | 4.42 | 19.27 | |
| (nM) | | | | | |

Note
that n.s. denotes that no saturation was observed in the assay.

Example 3—In Vivo Efficacy of NB0828 in Mouse Bladder MB49 and Colon CT26 Tumor Models The efficacy of NB0828 was tested in two separate tumor models, the bladder MB49 and colon CT26 tumor models. Briefly, 250,000 MB49 cells were injected intradermally into the flank of female C57BL/6 mice, or 50,000 CT26 cells injected intradermally in the flank of female Balb/c mice. 3 days following tumor implantation, mice were treated intraperitoneal with either NB0828 (50 mg/kg, 3QW) or Vehicle Control (PBS). Tumor volume was assessed twice weekly following caliper measurement and was calculated as (length×width)/2. Mice were euthanized when tumor size exceed 15 mm in any single direction or due to tumor ulceration as a humane endpoint.

Figure 2:
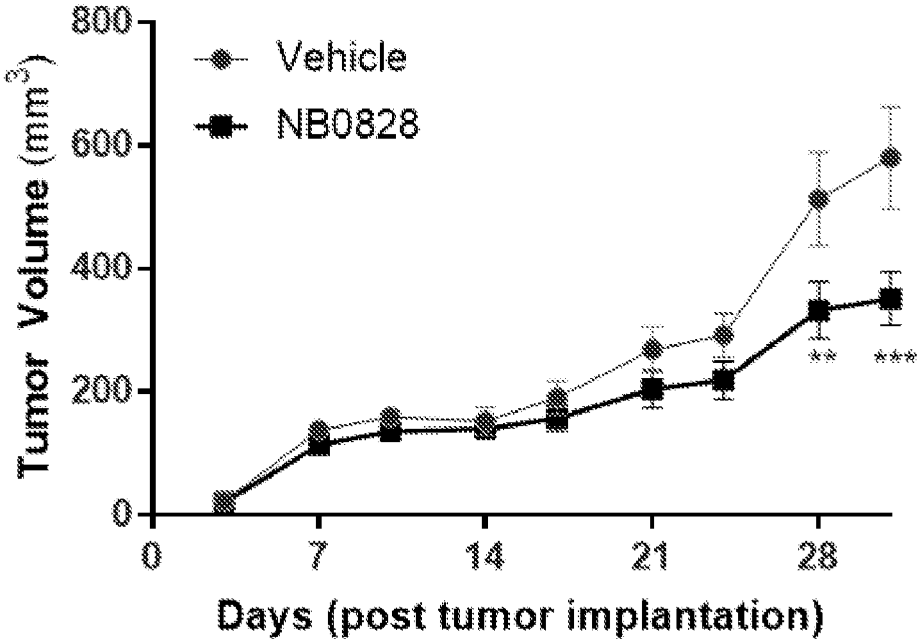
FIG. 2 illustrates tumor growth in the mouse MB49 bladder cancer model following treatment with NB0828 or vehicle control.
Figure 3:
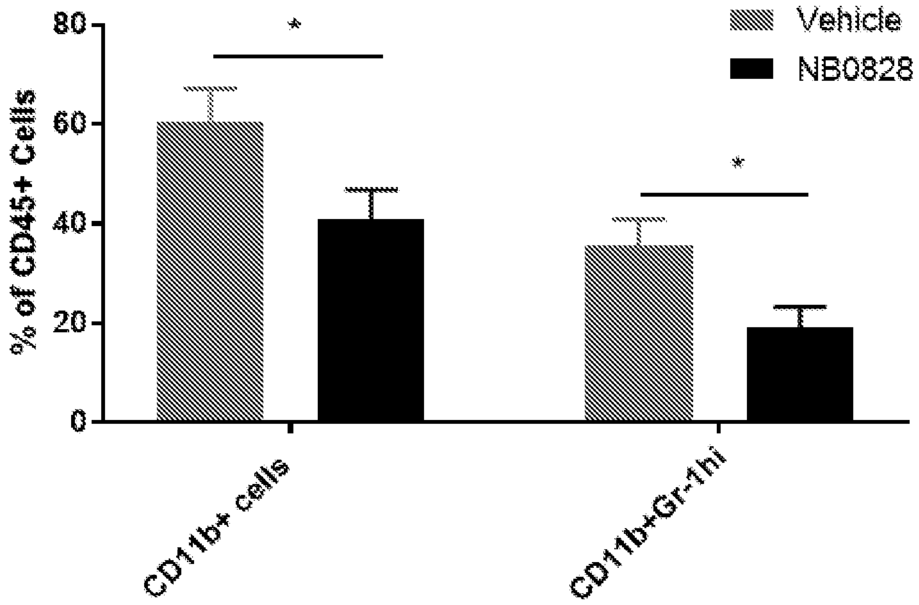
FIG. 3 illustrates the impact of NB0828 treatment on accumulation of intratumoral myeloid cells. MB49 tumor-bearing mice were treated with NB0828 or vehicle as described in FIG. 2. Data is presented as percent of total CD45+ immune infiltrate.
Figure 4:
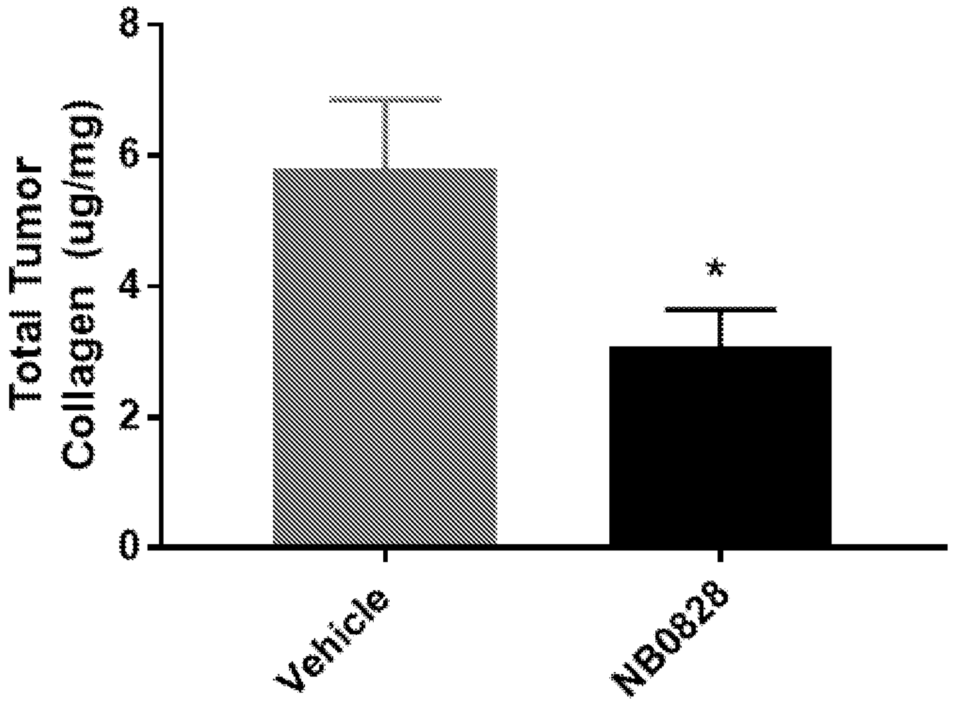
FIG. 4 illustrates changes in total tumor collagen content following treatment with NB0828. MB49 tumor-bearing mice were treated as described in FIG. 2, and total tumor collagen content of endpoint MB49 tumors was assessed as described in the methods.
Figure 5:
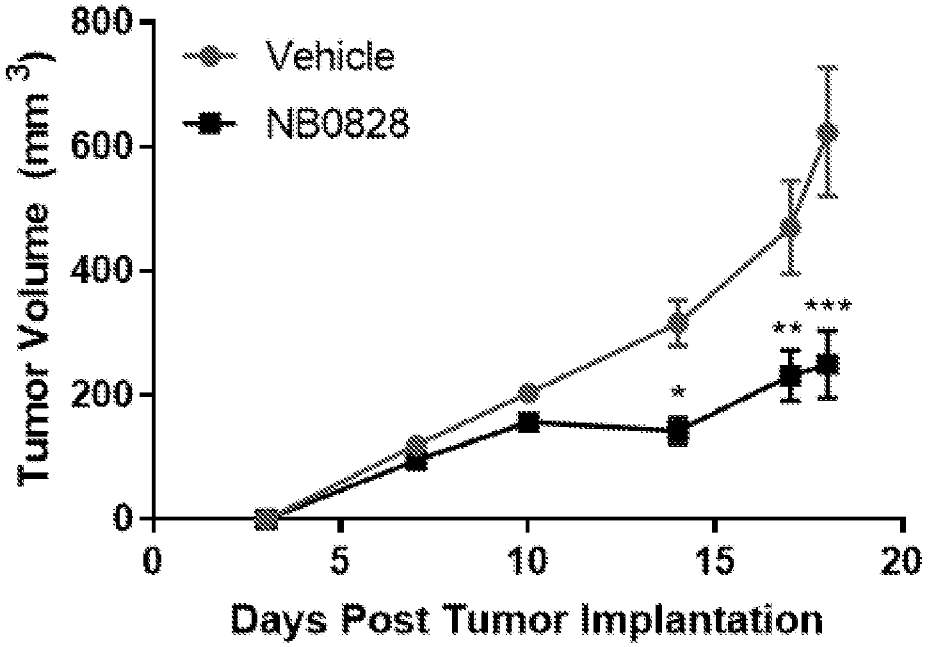
FIG. 5 illustrates tumor growth in the mouse CT26 colon cancer model following treatment with NB0828 or vehicle control.
Figure 6:
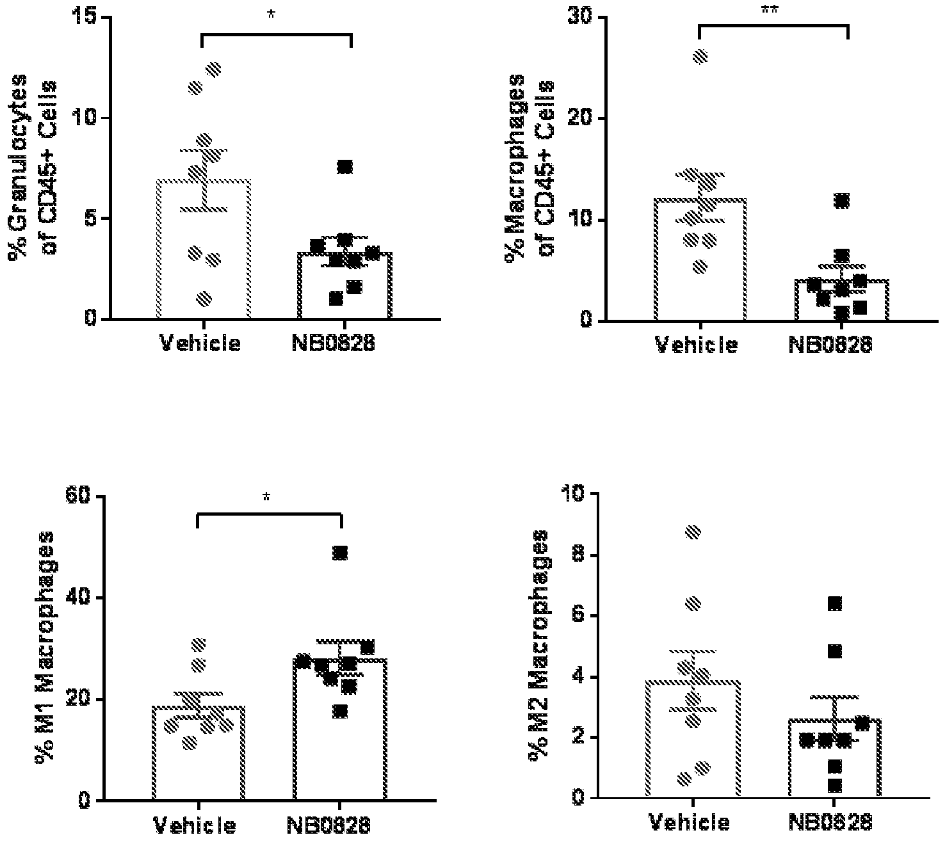
FIG. 6 illustrates reduced intratumoral accumulation of granulocytic cells/TAMs (Tumor associated macrophages) and macrophage skewing towards an M1 phenotype in NB0828 treated CT26 tumor-bearing mice.
Figure 7:
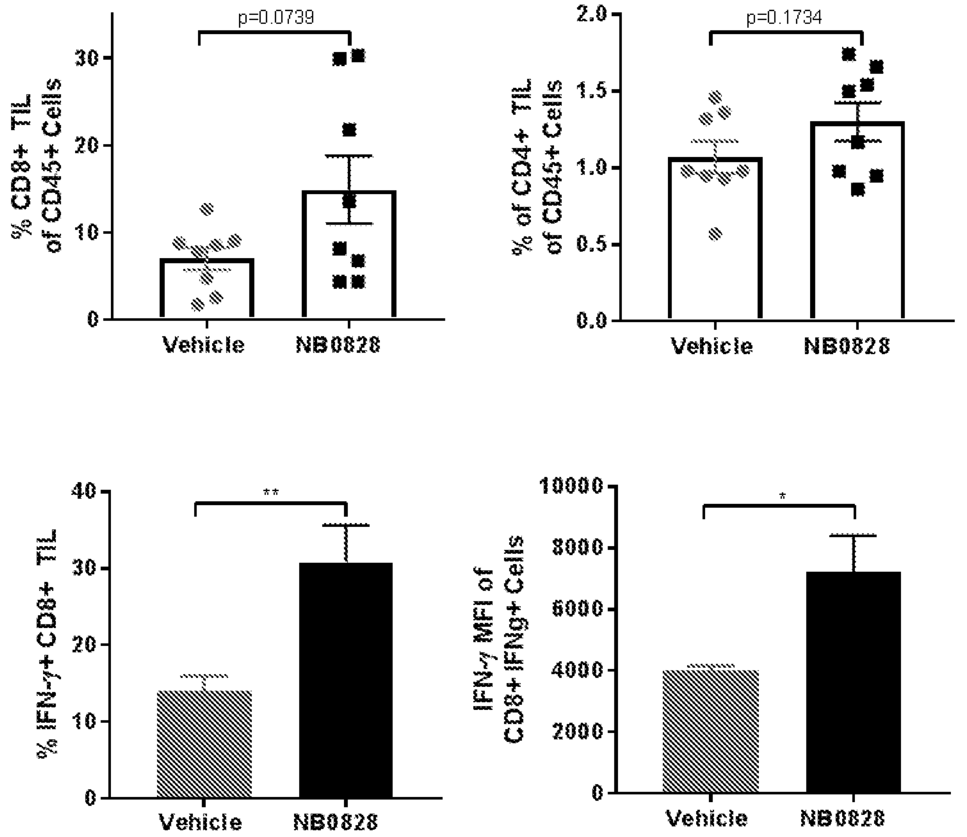
FIG. 7 illustrates increased accumulation of CD8+ and CD4+ tumor infiltrating lymphocytes (TILs) and enhanced CD8+ TIL function in NB0828 treated CT26 tumor-bearing mice.

As shown in FIG. 2 (MB49) and FIG. 5 (CT26), NB0828 had an effect in reducing tumor growth in both models. In the MB49 model this reduction in tumor growth was associated with a lower frequency of intratumoral granulocytic myeloid cells as shown in FIG. 3, and a lower collagen content, as shown in FIG. 4. As with the MB49 model, the CT26 model showed a reduction in granulocytic myeloid cells. In addition, NB0828 reduced the frequency of tumor infiltrating macrophages, and the macrophages that were present were skewed towards an M1 phenotype as a result of NB0828 treatment, as shown in FIG. 6. In the CT26 mouse model, NB0828 treatment was also associated with a higher frequency of tumor infiltrating CD8+ and CD4+ T cells, and increased CD8+ T cell function, as measured by the higher expression of interferon gamma as shown in FIG. 7.

Immunophenotyping

MB49 or CT26 tumor-bearing mice were treated with NB0828 or Vehicle Control beginning on day 3 as described. For the data shown, immunophenotyping was conducted on day 20 and day 18 post tumor implantation for MB49 and CT26, respectively. Tumors were excised, skin removed, and mechanically disrupted using a scalpel blade prior to being enzymatically digested using the Miltenyi mouse tumor dissociation enzyme mix. Digested samples were passed through a 40 μm strainer, washed in RPMI, followed by a second wash in RPMI+10% FBS. Cells were then resuspended for counting and a maximum of $2\times10^6$ leukocytes per sample was plated and stained for analysis by flow cytometry. For evaluation of CD8+ tumor infiltrating lymphocyte function in the CT26 model, digested single cell suspensions from tumors were stimulated with AH1 peptide [H2-$L^d$ restricted gp70 (423-431) MuLV epitope, the immunodominant CD8+ T cell epitope expressed by CT26 cells] in the presence of anti-CD28 and Brefeldin A for 5 hours at 37° C. Following stimulation, cells were stained to detect production of IFN-γ by CD8+ T cells using flow cytometry by standard surface/intracellular staining methods. The flow staining panels used to assess cell populations shown are included below in Table 4. A viability stain (Thermo Fisher, Live/Dead Fixable Violet Stain) was used to allow interrogation of only live cell events and the pan leukocyte marker CD45 was included to allow normalization of populations within the immune compartment. Immune populations of interest were defined phenotypically/functionally as follows: Total myeloid cells (CD45+CD11b+), granulocytes (CD45+CD11b+Gr-1 hi or CD45+CD11b+Ly6G+Ly6C lo), Macrophages (CD45+CD11b+Ly6G− Ly6C lo/neg F4/80+), M1 Macrophages (MHC II+ CD206−), M2 Macrophages (MHC II− CD206+), CD8+ TILs (CD45+CD11b− CD3+CD90.2+CD8+), CD4+ TILs (CD45+CD11b− CD3+CD90.2+CD4+), IFN-γ+CD8+ TILs (CD45+CD11b− CD3+CD8+ IFN-γ+). The Median Fluorescent Intensity (MFI) was used for determination of IFN-γ staining intensity from IFN-γ+CD8+ TIL.

TABLE 4

Antibody cocktails used to assess immune cell phenotype/function in MB49 and CT26 tumors

| | | | | |
|---|---|---|---|---|
| MB49 Staining Panel | | | | |
| MHC II - AF488 | iNOS-PE | CD11b-PerCP-Cy5.5 | PD-1-PE-Cy7 | Arginase-1-APC |
| Gr-1-AF700 | CD45-APC-Fire-750 | Live/Dead Violet | F4/80 BV510 | CD206 BV650 |
| CT26 Staining Panel - TIL Analysis | | | | |
| CD3-AF488 | PDGFR-α-PE | CD8a-PerCP-Cy5.5 | PD-1-PE-Cy7 | AH-1 Tetramer-APC |
| CD90.2-AF700 | CD45-APC-Fire-750 | Live/Dead Violet | CD4-BV510 | CD11b-BV650 |
| CT26 Staining Panel - TIL Function | | | | |
| CD3-AF488 | IFN-γ-PE | CD8a-PerCP-Cy5.5 | PD-1-PE-Cy7 | IL-2-AF647 |
| TNF-AF700 | CD45-APC-Fire-750 | Live/Dead Violet | CD4-BV510 | CD11b-BV650 |

TABLE 4-continued

| Antibody cocktails used to assess immune cell phenotype/function in MB49 and CT26 tumors | | | | |
|---|---|---|---|---|
| CT26 Staining Panel - Myeloid Cells | | | | |
| MHC II - AF488 | PD-L1-PE | CD11b-PerCP-Cy5.5 | Ly6C-PE-Cy7 | F4/80-AF647 |
| Ly6G-AF700 | CD45-APC-Fire-750 | Live/Dead Violet | CD40 BV510 | CD206 BV650 |

Collagen Content

Total collagen content of tumors was assessed by quantification of hydroxyproline using the Quickzyme Total Collagen Assay. For sample preparation, MB49 tumors were excised from tumor-bearing mice when tumors had reached endpoint and were snap frozen in liquid nitrogen and stored at −80 C prior to analysis. Tumor material was weighed and resuspended in 6M HCl at 200 mg tumor/ml HCl, vortexed and incubated at 95 C for 20 hrs. Tubes were cooled, centrifuged at 13,000 RPM for 10 minutes, and supernatant was collected. Supernatants were diluted in Milli Q water, followed by 4M HCl according to the manufacturer's recommended protocol and were plated in technical duplicates for detection of hydroxyproline using the supplied buffers and detection reagents. OD570 nm values were measured and compared to a standard curve generated using supplied collagen to calculate the amount of collagen in each sample. Calculated total collagen (μg) for each sample was divided by the total mass of tumor input (mg) to normalize the data across tumor samples.

Example 4—In Vivo Efficacy of NB0828 in the Mouse Colon MC38 Tumor Model

Figure 8:
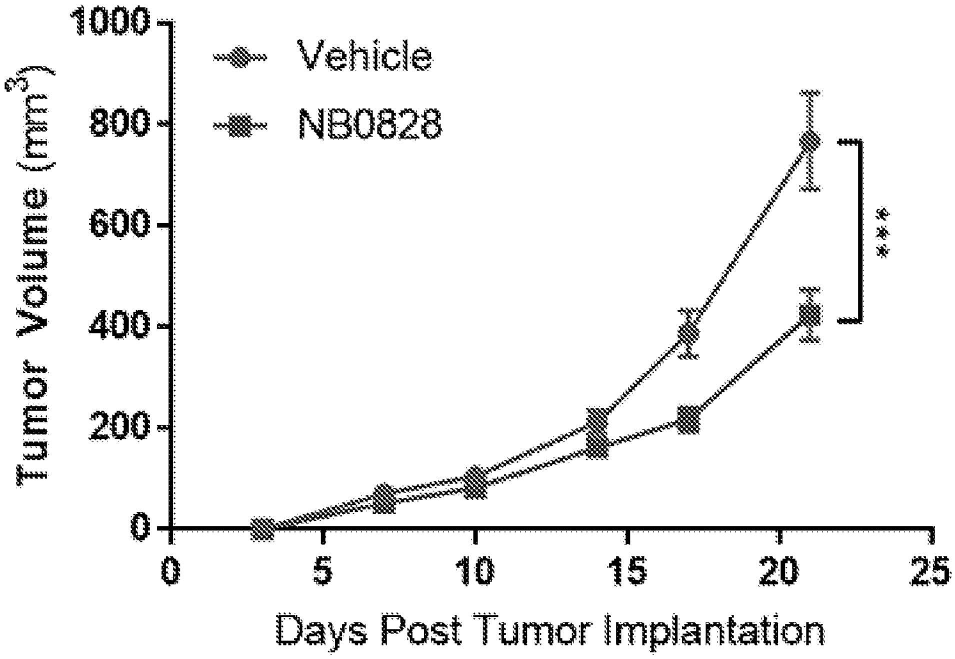
FIG. 8 illustrates tumor growth in the mouse MC38 colon cancer model following treatment with NB0828 or vehicle control.
Figure 9A:
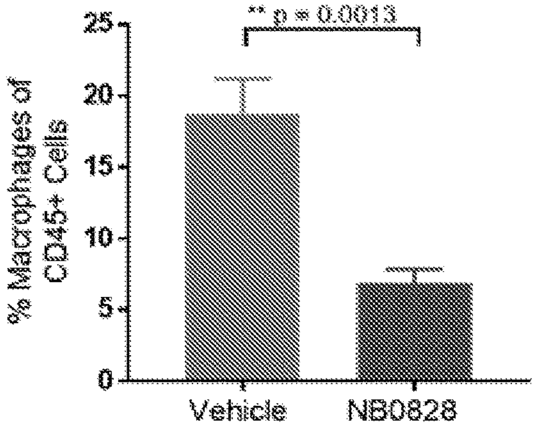
FIGS. 9A-9D illustrate that in the MC38 colon cancer model NB0828 decreases the overall amount of tumor associated macrophages (9A), while increasing the frequency of pro-inflammatory type I macrophages (9B), and CD8+ T cells (9C), and that NB0828 tumor efficacy is dependent on CD8+ T cells (9D).
Figure 9B:
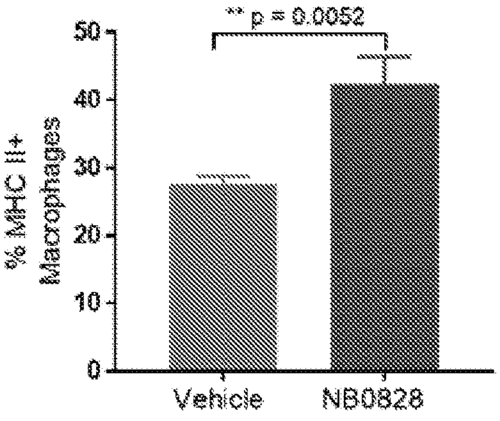
Figure 9C:
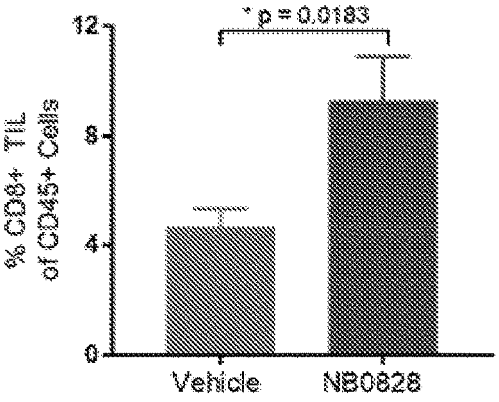
Figure 9D:
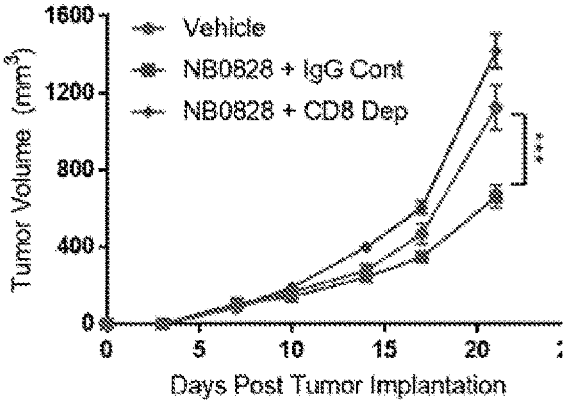

NB0828 was tested for its efficacy in reducing tumor growth in the mouse colon MC38 tumor model with the results shown in FIG. 8. Briefly, 200,000 MC38 cells were injected intradermally in the flank of female C57BL/6 mice. 3 days following tumor implantation, mice were treated intraperitoneal with either NB0828 (50 mg/kg, 3QW) or Vehicle Control (PBS). For depletion of CD8+ T cells, anti-mouse CD8a (Clone 2.43) or IgG Isotype control (Clone LTF-2) were delivered along with NB0828 for the first 6 doses (10 mg/kg, 3QW). Depletion of T cells was confirmed in the blood by flow cytometry using the flow staining panel listed in table 5. Tumor volume was measured using the same method as described for MB49 and CT26 models. NB0828 was effective in reducing tumor growth in the MC38 model (FIG. 8). NB0828 was also effective in altering the tumor microenvironment to increase CD8+ T cells, decrease the frequency of tumor-associated macrophages (TAMs) and increase the ratio of pro-inflammatory macrophages, as shown in FIGS. 9A and 9C. The efficacy of NB0828 to reduce tumor growth in this model was dependent on CD8+ T cells as depletion of CD8+ T cells during NB0828 treatment reversed the beneficial effect of NB0828, as shown in 9D. Overall, this data indicates that NB0828 effectively reduces tumor growth and increases CD8+ T cells to tumor sites, decreases TAMs and increases the pro-inflammatory M1 macrophage phenotype in infiltrating tumors.

Immunophenotyping

Tumors were excised, skin removed, and mechanically disrupted using a scalpel blade prior to being enzymatically digested using the Miltenyi mouse tumor dissociation enzyme mix (45 min incubation on shaking platform at 37° C.). Digested samples were passed through a 40 μm strainer, washed in RPMI, followed by a second wash in RPMI+10% FBS. Cells were then resuspended for counting and a maximum of $2\times10^6$ leukocytes per sample was plated and stained for analysis by flow cytometry. For evaluation of CD8+ tumor infiltrating lymphocyte (CD8+ TIL) function in the MC38 model, digested single cell suspensions from tumors (maximum $2\times10^6$ leukocytes per sample) were stimulated with p15E peptide [H2-$K^b$ restricted p15E (604-611) MuLV epitope expressed by MC38 tumors] in the presence of anti-CD28 and Brefeldin A for 5 hrs at 37° C. Following stimulation, cells were stained to detect production of IFN-γ by CD8+ T cells using flow cytometry by standard surface/intracellular staining methods using the eBioscience Intracellular Fix & Perm Buffer set. The flow staining panels used to assess cell populations shown are included in the table below. A viability stain (Thermo Fisher, Live/Dead Fixable Violet Stain) was used to allow interrogation of only live cell events and the pan leukocyte marker CD45 was included to allow normalization of populations within the immune compartment. For studies in MC38, reported immune populations of interest were defined phenotypically/functionally as follows: Total myeloid cells (CD45+CD11b+), Macrophages (CD45+CD11b+Ly6G− Ly6C lo/neg F4/80+), M1 Macrophages (MHC II+), M2 Macrophages (MHC II−), CD8+ TILs (CD45+CD11b− CD3+ SSC lo CD8+), IFN-γ+CD8+ TILs (CD45+CD11b− CD3+ SSC lo CD8+ IFN-γ+).

TABLE 5

| Antibody cocktails used to assess immune cell phenotype and function in MC38 tumors | | | | |
|---|---|---|---|---|
| MC38 Panel - Myeloid Cells | | | | |
| MHC II - AF488 | PD-L1-PE | CD11b-PerCP-Cy5.5 | Ly6C-PE-Cy7 | F4/80-AF647 |
| Ly6G-AF700 | CD45-APC-Fire-750 | L/D Violet | CD40-BV510 | CD206 BV650 |

TABLE 5-continued

| Antibody cocktails used to assess immune cell phenotype and function in MC38 tumors | | | | |
|---|---|---|---|---|
| MC38 Panel - T Cells | | | | |
| CD3-AF488 | IFN-γ-PE | CD8-PerCp-Cy5.5 | PD-1-PE-Cy7 | IL-2-AF647 |
| TNF-AF700 | CD45-APC-Fire-750 | L/D Violet | CD4-BV510 | CD11b-BV650 |
| MC38 Panel - Confirmation of CD8+ T cell Depletion | | | | |
| CD3-AF488 | | CD8-PerCp-Cy5.5 | | |
| | CD45-APC-Fire-750 | L/D Violet | CD4-BV510 | CD11b-BV650 |

Example 5—NB0828 Binds to the FAS2 Domain of Periostin (POSTN)

NB0828's binding region was investigated to further characterize the antibody.

Generation of BIGH3/POSTN Chimeric Proteins

Figure 10:
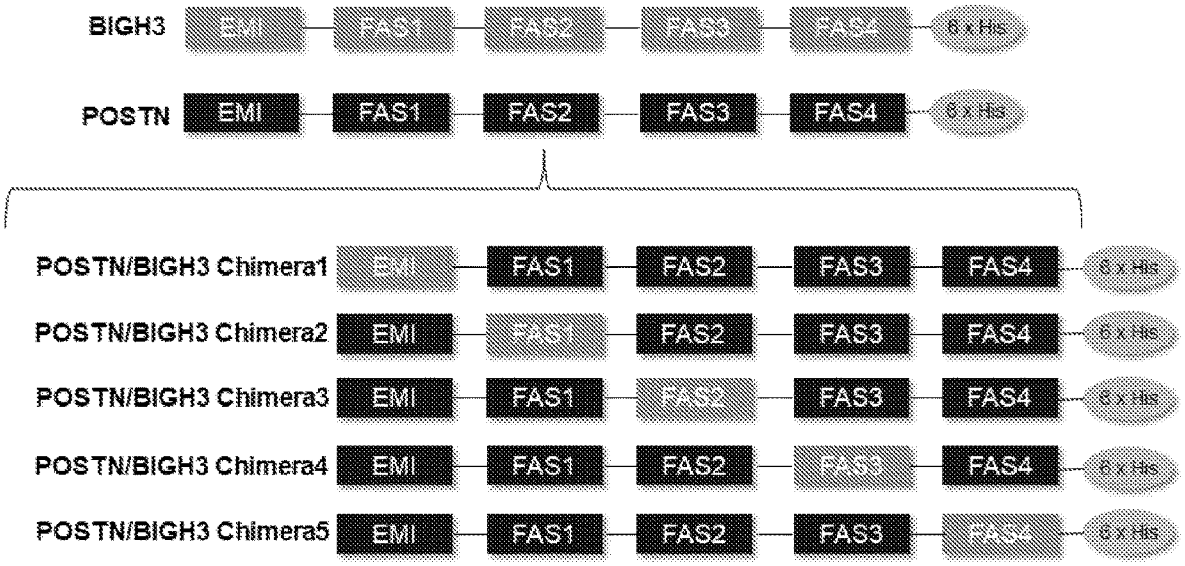
FIG. 10 illustrates a schematic for generating transforming growth factor beta-induced protein (BIGH3)/Periostin chimeras for epitope mapping studies.
Figure 11A:
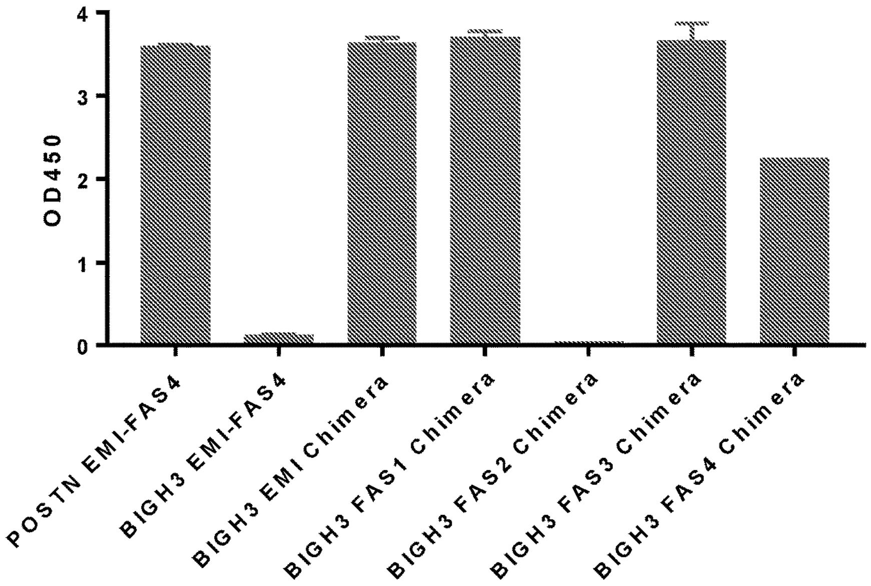

The closest homologous protein to periostin by sequence is transforming growth factor-beta-induced protein (BIGH3), which has a sequence homology of 48% within the EMI-FAS4 regions of the proteins. Although the sequence homology between the two proteins is low, the overall domain architecture is highly similar, comprising one EMI domain and four tandem fasciclin (FAS) domains. NB0828 binds with high affinity to periostin but does not bind to BIGH3. To further characterize the binding domain of NB0828, BIGH3/POSTN chimeric proteins were generated, whereby each domain of periostin was replaced with the corresponding domain of BIGH3, generating five BIGH3/POSTN chimeras (FIG. 10). NB0828 binding studies were performed on these proteins by ELISA. As shown in FIG. 11A, NB0828 retains binding to all BIGH3/POSTN chimeras except for the FAS2 chimera. This observable loss of binding when replacing the POSTN FAS2 domain with the BIGH3 FAS2 domain indicates that NB0828 binds to the FAS2 domain of POSTN.

Generation of POSTN FAS2 Variants

The FAS2 domain of periostin is a conformational structure composed of 132 amino acids. Single amino acid substitution (alanine) variants in various positions across the FAS2 domain were generated to further define the NB0828 epitope or binding region and identify critical contact residues (Table 6). Residues were identified for mutagenesis based on surface exposure in MOE, a computational analysis tool, using the published crystal structure (Liu et al, 2018; PDB #5YJG).

TABLE 6

| FAS2 Variants Protein | |
|---|---|
| Protein ID | AA Substitution |
| NB1187 | Q238A |
| NB1188 | D239A |
| NB1189 | E242A |
| NB1190 | D245A |
| NB1191 | D246A |
| NB1192 | S248A |
| NB1193 | S249A |
| NB1194 | F250A |

TABLE 6-continued

| FAS2 Variants Protein | |
|---|---|
| Protein ID | AA Substitution |
| NB1195 | R251A |
| NB1196 | I255A |
| NB1197 | T256A |
| NB1198 | D258A |
| NB1199 | E261A |
| NB1200 | R265A |
| NB1201 | P274A |
| NB1202 | N276A |
| NB1203 | E280A |
| NB1204 | P283A |
| NB1205 | R284A |
| NB1206 | G285A |
| NB1207 | E288A |
| NB1208 | M291A |
| NB1209 | K294A |
| NB1210 | E298A |
| NB1238 | T235A |
| NB1239 | L260A |
| NB1240 | D266A |
| NB1241 | F279A |
| NB1242 | K281A |
| NB1243 | L287A |
| NB1244 | R289A |
| NB1245 | D293A |
| NB1246 | V295A |
| NB1247 | S297A |
| NB1248 | K302A |

Figure 11B:
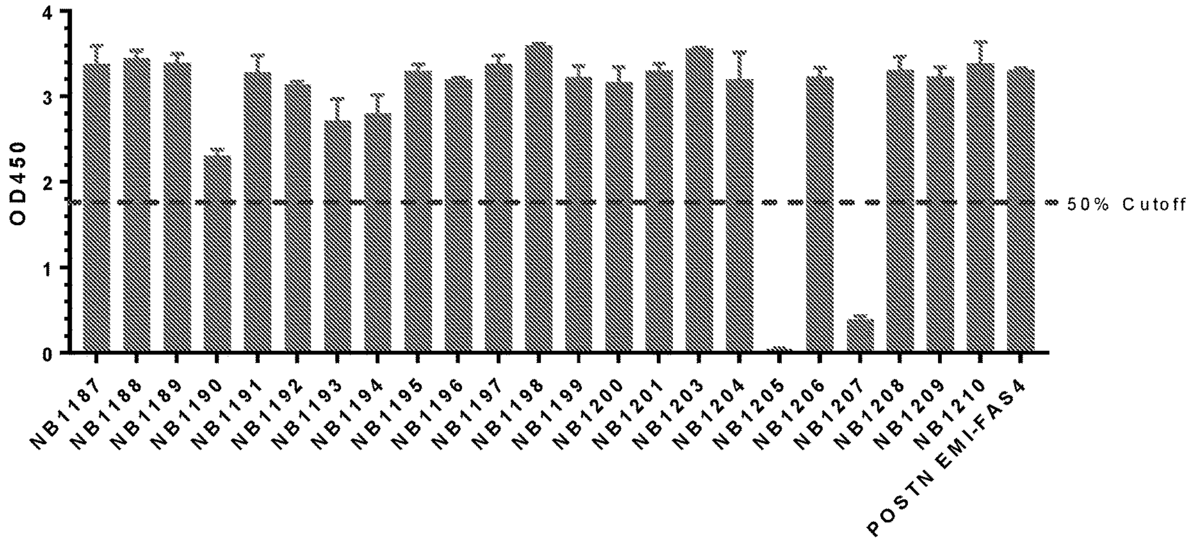
Figure 11C:
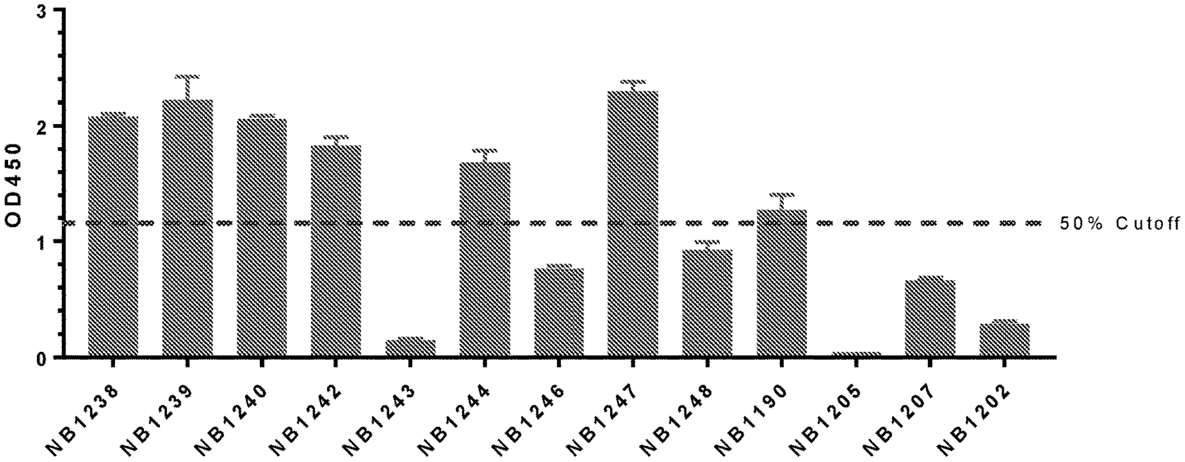
Figure 12:
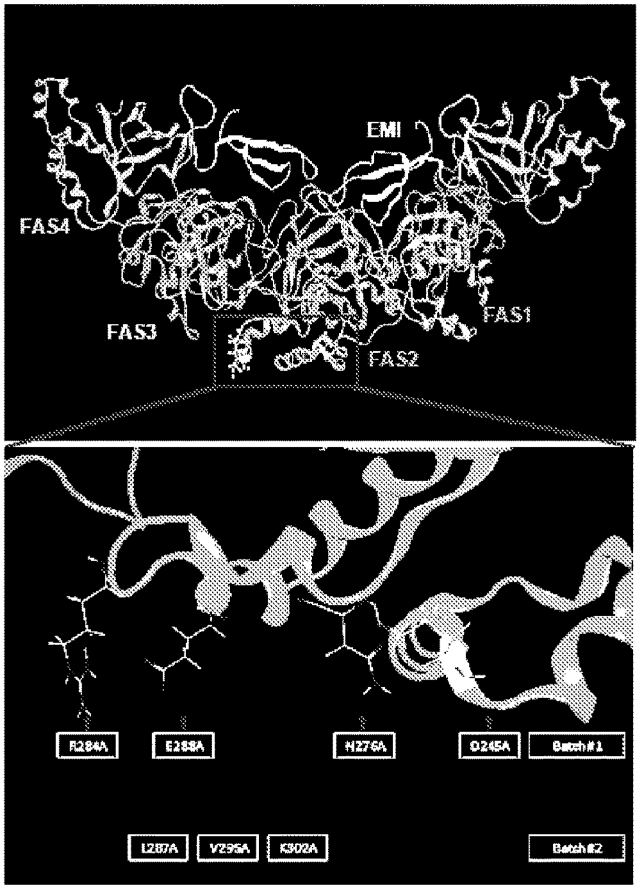
FIG. 12 illustrates the crystal structure of dimeric POSTN EMI-FAS4 with the location of the NB0828 epitope boxed and magnified in the bottom half.

23 alanine variants that spanned residues across the entire FAS2 domain were generated in the initial round. NB0828 binding studies were performed on these variants and variants that had a >50% loss from the max signal within the assay were identified as residues that are critical for binding. FIG. 11B illustrates the results from that screen. Two variants that represented critical amino acids for NB0828 binding were identified: NB1205 (R284A) and NB1207 (E288A). Given the close proximity of these two amino acids (FIG. 12), a second round of 11 additional variants were generated, focusing more specifically on residues within this region. FIG. 11C illustrates the results from the second screen. Based on the ELISA results from the second screen, an additional four variants that represented amino acids critical for NB0828 binding were identified: NB1243 (L287A), NB1246 (V295A), NB1248 (K302A) and NB1202 (N276A). Notably, NB1190 (D245A), which was very close to the >50% loss from the max signal cutoff but did not fall below, is located on a separate loop from the remaining residues but forms a contact point with N276 within the FAS2 domain and on the NB0828 binding loop (FIG. 12). Given that N276 was identified as a critical residue for NB0828 binding, the D245 residue may either also be a contact residue for NB0828 or provide structural integrity to the NB0828 epitope loop that is important for binding.

NB0828 Affinity Determination Across Species

NB0828's binding affinity was determined across human, mouse, rat, and cyno species. NB0828 affinities were determined using the octet red system. Briefly, anti-human Fc (AHC) biosensors were used to capture NB0828, followed by association of titrating amounts of either recombinant human, mouse, rat, or cyno periostin (100 nM→0 nM; 1:2 dilutions). Recombinant human, mouse, and rat periostin was purchased commercially from R&D systems, whereas cyno periostin was made internally. The results indicate that the affinities of NB0828 to periostin across the four species are highly similar, ranging from 0.1-0.5 nM. This data strongly supports the epitope mapping experiments detailed above, as the sequence identity in the described NB0828 binding loop was 100% across the four species.

TABLE 7

NB0828 affinities for human, cyno, mouse, and rat periostin

| Species | KD (M) | kon(1/Ms) | kdis(1/s) |
|---|---|---|---|
| HuPOSTN | 3.51E−10 | 7.02E+05 | 2.46E−04 |
| CynoPOSTN | 2.65E−10 | 7.94E+05 | 2.11E−04 |
| MoPOSTN | 1.14E−10 | 6.70E+05 | 7.64E−05 |
| RatPOSTN | 5.40E−10 | 7.27E+05 | 3.93E−04 |

Example 6—NB0828 does not Block Periostin Binding to Tenascin C and Type 1 Collagen but Blocks Cell Attachment To determine whether NB0828 blocks periostin binding to extracellular proteins, tenascin C and type I collagen, a competitive ELISA assay was performed. Recombinant human periostin (2 ng/mL) was coated on maxisorp plates overnight at 4° C. The next day, plates were blocked with casein blocking buffer for 1 hr at 37° C. In order to determine the binding EC80 for recombinant human tenascin C and human collagen type I, proteins were biotinylated 10:1 using EZ-Link™ NHS-PEG4-Biotin (Fisher), and titrations of each biotinylated protein were added to the plates and incubated for 1 hr at RT. Plates were washed 4× with PBST followed by detection using Avidin-HRP for 30 min. Plates were then washed again with 4×PBST and developed using TMB substrate and 1M HCl. The $EC_{80}$ for each protein was determined using Graphpad Prism 7 software. For the competitive ELISA, titrations of NB0828, control IgG or PBST were added to the plate and incubated for 30 min shaking at RT. Plates were then washed 4× with PBST, and the binding EC80 concentration of either biotinylated-tenascin C (0.9 nM, 13A, left), or collagen (100 nM, 13B, left) or a pre-mixed blocking control was added to the plate. The pre-mixed blocking control was prepared by mixing the EC80 concentration of biotinylated protein with a titration of recombinant human Periostin, incubated shaking for 30 min at RT prior to being added to the plate. Plates were then incubated for 1 h shaking at RT, and washed, detected and developed as described above.

Figure 13A:
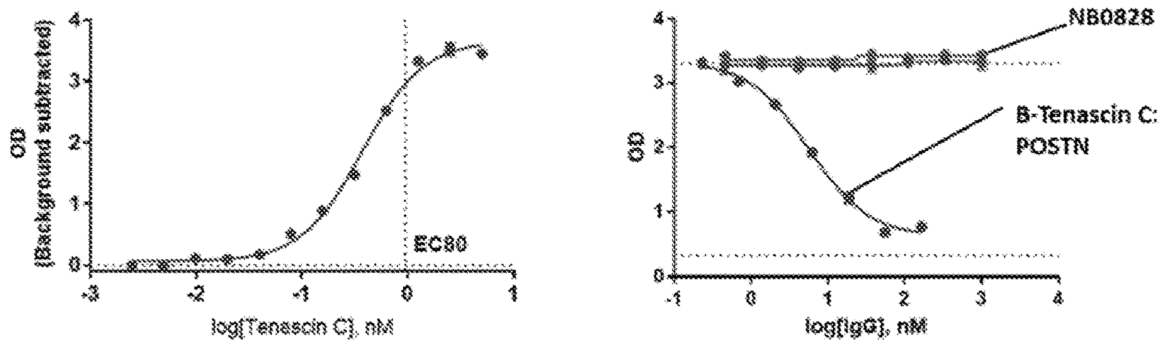
FIGS. 13A and 13B illustrate binding EC80 of human tenascin C to periostin and NB0828 function blocking activity (13A), and binding EC80 of human type I collagen to periostin and NB0828 function blocking activity (13B).
Figure 13B:
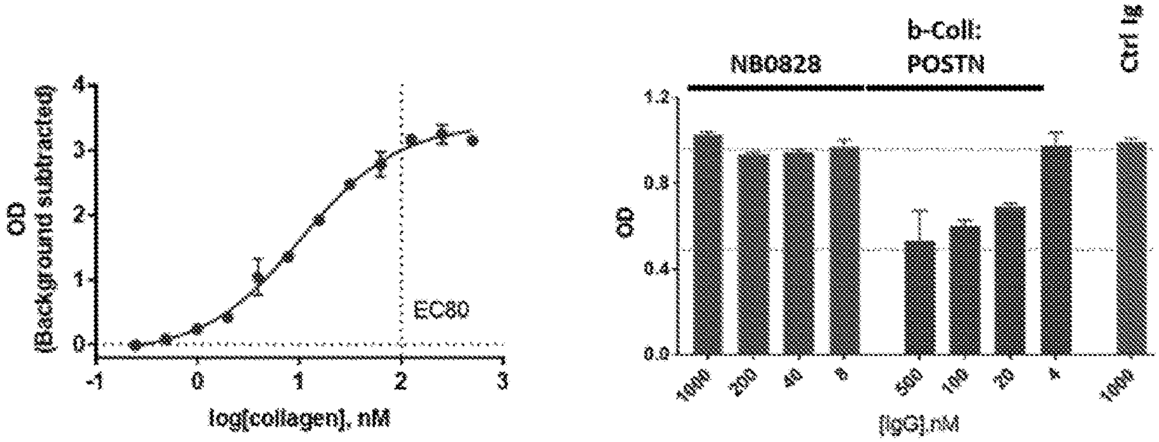

Tenascin C and type I collagen bound to periostin with an $EC_{80}$ binding of 0.9 nM and 100 nM, respectively (FIGS. 13A and 13B). As shown in FIGS. 13A and 13B, NB0828 did not inhibit periostin binding to tenascin C and type I collagen, in contrast to the premixed positive control. Taken together, these data indicate that NB0828 does not block the interaction of periostin to extracellular matrix proteins, tenascin C and type I collagen.

Figure 14A:
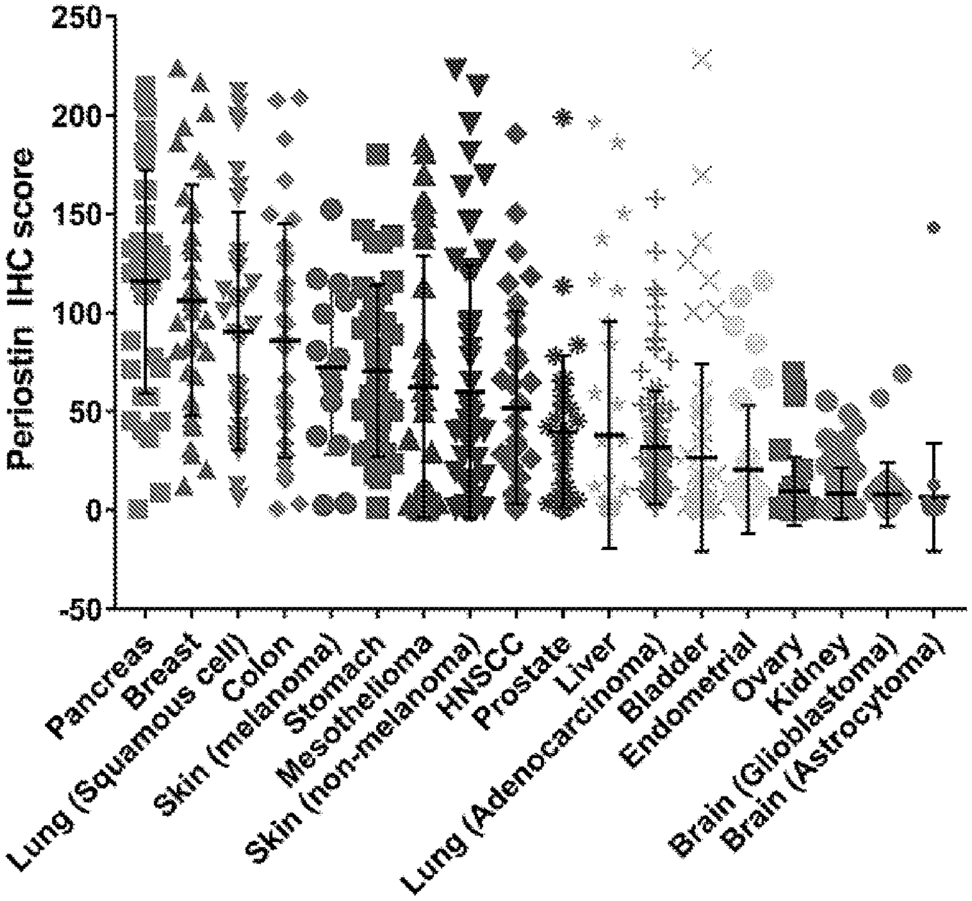
FIG. 14A depicts the prevalence of periostin expression in various tumor types as measured by immunohistochemistry.
Figure 14B:
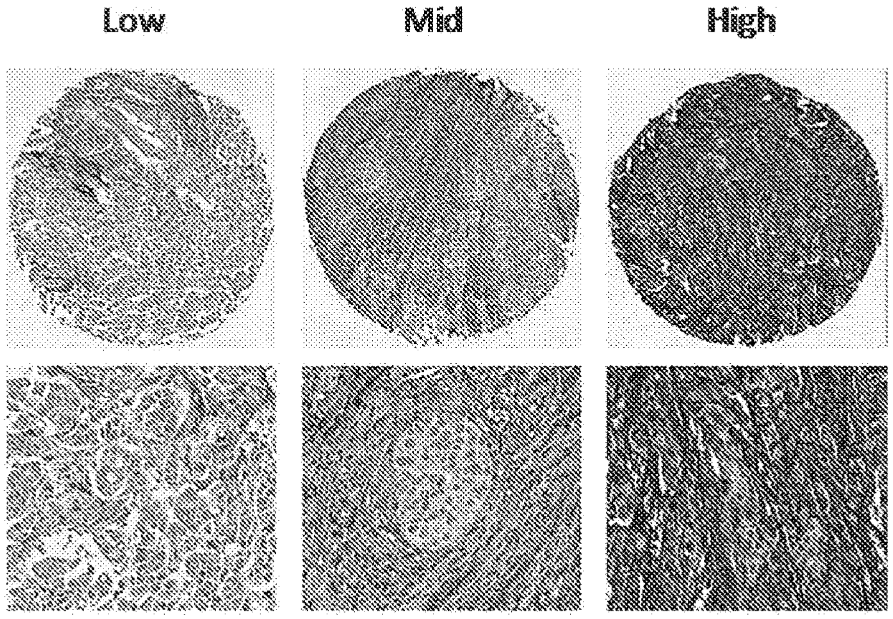
FIG. 14B shows representative depictions of IHC staining on periostin low, medium, and high expressing breast cancer samples.

Example 7—Immunohistochemistry (IHC) Evaluation of Periostin Expression Across Human Tumor Indications To assess periostin expression levels across different human cancers, an immunohistochemistry (IHC) prevalence study was performed. Tissue microarrays (TMA) comprising 18 tumor indications and approximately 750 individual samples were evaluated for periostin expression. Samples were stained with anti-periostin antibody EPR20806 (Abcam cat id: ab215199, lot id: GR3192974-3) diluted 1:50. Staining was quantified using digital pathology methods (HALO, Indica labs) to calculate an IHC score (IHC Score=[% low intensity staining area *1]+[% intermediate intensity staining area *2]+[% high intensity staining area *3]). A cut-point for low/high periostin staining was calculated as a periostin IHC score of 50, based on the approximate average periostin IHC score across all the samples. The prevalence study demonstrated a range of periostin staining across and within tested indications, with pancreatic, breast and squamous lung cancers showing the highest levels of periostin staining (FIG. 14A). Periostin high tumors were present in all indications, albeit at differing frequency (FIG. 14A). Representative IHC images of periostin expression in breast cancer is shown in FIG. 14B. Taken together, these data demonstrate that periostin is broadly expressed across multiple tumor types.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

TABLE 8

Sequence listings provided herein

| SEQ ID NO: | Sequence | Origin |
|---|---|---|
| 1 | GYTFTSYG | |
| 2 | ISAYNGNT | |
| 3 | ISAYSGNT | |
| 4 | ISAYQGNT | |
| 5 | ISAYTGNT | |
| 6 | ISAYDGNT | |
| 7 | DILVVPFDY | |
| 8 | DVLVVPFDY | |
| 9 | DMLVVPFDY | |
| 10 | SSDIGSNR | |
| 11 | SND | |
| 12 | AAWDDSLSTYV | |
| 13 | QVQLVQSGAEVKKPGASVKVSCKASGYTFTSYGISWVRQAPGQGLEWM GWISAYNGNTNYAQKLQGRVTMTTDTSTSTAYMELRSLRSDDTAVYYC ARDMLVVPFDYWGQGTLVTVSS | |
| 14 | QSVLTQSSSASGTPGQTVTVSCSGSSSDIGSNRVNWYQQLPGTAPKLLIYS NDQRPSGVPDRFSGSKSGTSASLAISGLQSADEADYYCAAWDDSLSTYVF GSGTKVTVL | |
| 15 | MIPFLPMFSLLLLLIVNPINANNHYDKILAHSRIRGRDQGPNVCALQQILG TKKKYFSTCKNWYKKSICGQKTTVLYECCPGYMRMEGMKGCPAVLPID HVYGTLGIVGATTTQRYSDASKLREEIEGKGSFTYFAPSNEAWDNLDSDI RRGLESNVNVELLNALHSHMINKRMLTKDLKNGMIIPSMYNNLGLFINH YPNGVVTVNCARIIHGNQIATNGVVHVIDRVLTQIGTSIQDFIEAEDDLSSF RAAAITSDILEALGRDGHFTLFAPTNEAFEKLPRGVLEREVIGDKVASEAL MKYHILNTLQCSESIIVIGGAVFETLEGNTIEIGCDGDSITVNGIKMVNKKDI VTNNGVIHLIDQVLIPDSAKQVIELAGKQQTTFTDLVAQLGLASALRPDG EYTLLAPVNNAFSDDTLSMDQRLLKLILQNHILKVKVGLNELYNGQILETI GGKQLRVFVYRTAVCIENSCMEKGSKQGRNGAIHIFREIIKPAEKSLHEKL KQDKRFSTFLSLLEAADLKELLTQPGDWTLFVPTNDAFKGMTSEEKEILIR DKNALQNIILYHLTPGVFIGKGFEPGVTNILKTTQGSKIFLKEVNDTLLVN ELKSKESDEVITTNGVIHVVDKLLYPADTPVGNDQLLEILNKLIKYIQIKFV RGSTFKEIPVTVYTTKIITKVVEPKIKVIEGSLQPIIKTEGPTLTKVKIEGEPE FRLIKEGETITEVIHGEPIIKKYTKIIDGVPVEITEKETREERIITGPEIKYTR ISTGGGETEETLKKLLQEEVTKVTKFIEGGDGHLFEDEEIKRLLQGDTPVRK LQANKKVQGSRRRLREGRSQ | |
| 16 | ISAYXGNT | |
| 17 | DXLVVPFDY | |

What is claimed is:

1. A recombinant antibody or antigen binding fragment thereof that binds periostin, wherein the antibody or antigen binding fragment thereof comprises:

a) an immunoglobulin heavy chain complementarity determining region (CDR) 1 (CDR-H1) comprising the amino acid sequence of SEQ ID NO: 1 (GYTFTSYG);

b) an immunoglobulin heavy chain CDR2 (CDR-H2) comprising the amino acid sequence of any one of SEQ ID NOs: 2 (ISAYNGNT), 3 (ISAYSGNT), 4(ISAYQGNT), 5 (ISAYTGNT), or 6 (ISAYDGNT);

c) an immunoglobulin heavy chain CDR3 (CDR-H3) comprising the amino acid sequence of any one of SEQ ID NOs: 7 (DILVVPFDY), 8 (DVLVVPFDY), or 9 (DMLVVPFDY);

d) an immunoglobulin light chain CDR1 (CDR-L1) comprising the amino acid sequence of SEQ ID NO: 10 (SSDIGSNR);

e) an immunoglobulin light chain CDR2 (CDR-L2) comprising the amino acid sequence of SEQ ID NO: 11 (SND); and f) an immunoglobulin light chain CDR3 (CDR-L3) comprising the amino acid sequence of SEQ ID NO: 12 (AAWDDSLSTYV).

2. The recombinant antibody or antigen binding fragment thereof of claim 1, wherein the recombinant antibody or antigen binding fragment thereof comprises:

a) an immunoglobulin heavy chain CDR1 (CDR-H1) comprising the amino acid sequence of SEQ ID NO: 1 (GYTFTSYG);

b) an immunoglobulin heavy chain CDR2 (CDR-H2) comprising the amino acid sequence of SEQ ID NO: 2 (ISAYNGNT);

c) an immunoglobulin heavy chain CDR3 (CDR-H3) comprising the amino acid sequence of SEQ ID NO: 9 (DMLVVPFDY);

d) an immunoglobulin light chain CDR1 (CDR-L1) comprising the amino acid sequence of SEQ ID NO: 10 (SSDIGSNR);

e) an immunoglobulin light chain CDR2 (CDR-L2) comprising the amino acid sequence of SEQ ID NO: 11 (SND); and f) an immunoglobulin light chain CDR3 (CDR-L3) comprising the amino acid sequence of SEQ ID NO: 12 (AAWDDSLSTYV).

3. The recombinant antibody or antigen binding fragment thereof of claim 1, wherein the recombinant antibody or antigen binding fragment thereof is human, chimeric, or humanized.

4. The recombinant antibody or antigen binding fragment thereof of claim 1, wherein the recombinant antibody or antigen binding fragment thereof is an IgG antibody.

5. The recombinant antibody or antigen binding fragment thereof of claim 1, wherein the recombinant antibody or antigen binding fragment thereof comprises an IgG4 constant region comprising one or more mutations or sets of mutations selected from: N434A, N434H, T307A/E380A/N434A, M252Y/S254T/T256E, 433K/434F/436H, T250Q, T250F, M428L, M428F, T250Q/M428L, N434S, V308W, V308Y, V308F, M252Y/M428L, D259I/V308F, M428L/V308F, Q311V/N434S, T307Q/N434A, E258F/V427T, S228P, L235E, S228P/L235E/R409K, S228P/L235E, K370Q, K370E, deletion of G446, deletion of K447, and combinations thereof, wherein said mutations are numbered according to the EU numbering system.

6. The recombinant antibody or antigen binding fragment thereof of claim 1, wherein the recombinant antibody or antigen binding fragment thereof comprises an IgG4 constant region comprising the mutations S228P, F234A, and L235A, wherein said mutations are numbered according to the EU numbering system.

7. The recombinant antibody or antigen binding fragment thereof of claim 1, wherein the recombinant antibody or antigen binding fragment thereof is or comprises a Fab, $F(ab)_2$, or a single chain variable fragment (scFv).

8. The recombinant antibody or antigen binding fragment thereof of claim 1, comprising an immunoglobulin heavy chain variable region and an immunoglobulin light chain variable region:

a) wherein the immunoglobulin heavy chain variable region comprises an amino acid sequence which is at least 90% identical to SEQ ID NO: 13; and b) wherein the immunoglobulin light chain variable region comprises an amino acid sequence which is at least 90% identical to SEQ ID NO: 14;

wherein the amino acid residue of the heavy chain variable region that corresponds to residue number 55 of SEQ ID NO: 13 is asparagine, serine, glutamine, threonine, or aspartic acid, or wherein the amino acid residue of the heavy chain variable region that corresponds to residue number 100 of SEQ ID NO: 13 is methionine, isoleucine, or valine.

9. The recombinant antibody or antigen binding fragment thereof of claim 1, wherein the recombinant antibody or antigen binding fragment thereof when bound to periostin contacts one of the following amino acid residues: N276, R284, E288, L287, V295, and K302 of SEQ ID NO: 15.

10. The recombinant antibody or antigen binding fragment thereof of claim 1, wherein the recombinant antibody or antigen binding fragment thereof when bound to periostin contacts two, three, four, or five of the following amino acid residues: N276, R284, E288, L287, V295, and K302 of SEQ ID NO: 15.

11. The recombinant antibody or antigen binding fragment thereof of claim 1, wherein the recombinant antibody or antigen binding fragment thereof when bound to periostin contacts all of the following amino acid residues: N276, R284, E288, L287, V295, and K302 of SEQ ID NO: 15.

12. The recombinant antibody or antigen binding fragment thereof of claim 1, comprising an immunoglobulin heavy chain variable region and an immunoglobulin light chain variable region:

a) wherein the immunoglobulin heavy chain variable region comprises an amino acid sequence which is at least 95% identical to SEQ ID NO: 13; and b) wherein the immunoglobulin light chain variable region comprises an amino acid sequence which is at least 95% identical to SEQ ID NO: 14;

wherein the amino acid residue of the heavy chain variable region that corresponds to residue number 55 of SEQ ID NO 13: is asparagine, serine, glutamine, threonine, or aspartic acid, or wherein the amino acid residue of the heavy chain variable region that corresponds to residue number 100 of SEQ ID NO: 13 is methionine, isoleucine, or valine.

13. The recombinant antibody or antigen binding fragment thereof of claim 1, comprising an immunoglobulin heavy chain variable region and an immunoglobulin light chain variable region:

a) wherein the immunoglobulin heavy chain variable region comprises an amino acid sequence which is at least 97% identical to SEQ ID NO: 13; and b) wherein the immunoglobulin light chain variable region comprises an amino acid sequence which is at least 97% identical to SEQ ID NO: 14.

14. A recombinant antibody or antigen binding fragment thereof that binds periostin, comprising an immunoglobulin heavy chain variable region and an immunoglobulin light chain variable region:

a) wherein the immunoglobulin heavy chain variable region comprises the amino acid sequence of SEQ ID NO: 13; and b) wherein the immunoglobulin light chain variable region comprises the amino acid of SEQ ID NO: 14.

15. The recombinant antibody or antigen binding fragment thereof of claim 12, wherein the recombinant antibody or antigen binding fragment thereof is human, humanized, or chimeric.

16. The recombinant antibody or antigen binding fragment thereof of claim 12, wherein the recombinant antibody or antigen binding fragment thereof is an IgG antibody.

17. The recombinant antibody or antigen binding fragment thereof of claim 12, wherein the recombinant antibody or antigen binding fragment thereof comprises an IgG4 constant region comprising one or more mutations or sets of mutations selected from: N434A, N434H, T307A/E380A/N434A, M252Y/S254T/T256E, 433K/434F/436H, T250Q, T250F, M428L, M428F, T250Q/M428L, N434S, V308W, V308Y, V308F, M252Y/M428L, D259I/V308F, M428L/V308F, Q311V/N434S, T307Q/N434A, E258F/V427T, S228P, L235E, S228P/L235E/R409K, S228P/L235E, K370Q, K370E, deletion of G446, deletion of K447, and combinations thereof, wherein said mutations are numbered according to the EU numbering system.

18. The recombinant antibody or antigen binding fragment thereof of claim 12, wherein the recombinant antibody or antigen binding fragment thereof comprises an IgG4 constant region comprising the mutations S228P, F234A, and L235A, wherein said mutations are numbered according to the EU numbering system.

19. The recombinant antibody or antigen binding fragment thereof of claim 12, wherein the recombinant antibody or antigen binding fragment thereof is or comprises a Fab, $F(ab)_2$, or a single chain variable fragment (scFv).

20. The recombinant antibody or antigen binding fragment thereof of claim 1, wherein the antibody has an IC50 of about 50 nanomolar or less than 50 nanomolar in a cell adhesion assay performed with human lung fibroblast cells and/or mouse fibroblast cells.

21. A nucleic acid encoding the recombinant antibody or antigen binding fragment thereof of claim 1.

22. A cell line comprising the nucleic acid of claim 21.

23. The cell line of claim 22, wherein the cell line is a Chinese Hamster Ovary cell line.

24. A pharmaceutical composition comprising the recombinant antibody or antigen binding fragment thereof of claim 1 and a pharmaceutically acceptable excipient, carrier, or diluent.

25. The pharmaceutical composition of claim 24, wherein said pharmaceutical composition is formulated for intravenous administration.

26. The pharmaceutical composition of claim 24, wherein said pharmaceutical composition is formulated for subcutaneous administration.

27. The pharmaceutical composition of claim 24, wherein said pharmaceutical composition is formulated for intratumoral administration.

28. A method comprising administering to an individual the recombinant antibody or antigen binding fragment thereof of claim 1.

29. A method of making a composition, comprising admixing the recombinant antibody or antigen binding fragment thereof of claim 1 and a pharmaceutically acceptable excipient, carrier, or diluent.

30. A method of producing the recombinant antibody or antigen binding fragment thereof of claim 1 comprising incubating a cell line comprising a nucleic acid encoding the recombinant antibody or antigen binding fragment of claim 1 in a cell culture medium under conditions sufficient to allow expression and secretion of the recombinant antibody or antigen binding fragment.

31. A recombinant antibody or antigen binding fragment thereof that binds periostin, comprising an immunoglobulin heavy chain variable region and an immunoglobulin light chain variable region, wherein the amino acid sequence of the immunoglobulin heavy chain variable region consists of the amino acid sequence of SEQ ID NO: 13; and wherein the amino acid sequence of the immunoglobulin light chain variable region consists of the amino acid of SEQ ID NO: 14.

32. A pharmaceutical composition comprising the recombinant antibody or antigen binding fragment thereof of claim 31 and a pharmaceutically acceptable excipient, carrier, or diluent.

* * * * *

SEQUENCE LISTING

<160> NUMBER OF SEQ ID NOS: 18

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Ser Tyr Gly 1 5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2

Ile Ser Ala Tyr Asn Gly Asn Thr
1 5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 3

Ile Ser Ala Tyr Ser Gly Asn Thr
1 5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

Ile Ser Ala Tyr Gln Gly Asn Thr
1 5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Ile Ser Ala Tyr Thr Gly Asn Thr
1 5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Ile Ser Ala Tyr Asp Gly Asn Thr
1 5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Asp Ile Leu Val Val Pro Phe Asp Tyr
1 5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Asp Val Leu Val Val Pro Phe Asp Tyr
1 5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Asp Met Leu Val Val Pro Phe Asp Tyr
1 5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Ser Ser Asp Ile Gly Ser Asn Arg
1 5

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Ser Asn Asp
1

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Ala Ala Trp Asp Asp Ser Leu Ser Thr Tyr Val
1 5 10

<210> SEQ ID NO 13

<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Met Leu Val Val Pro Phe Asp Tyr Trp Gly Gln Gly Thr
100 105 110

Leu Val Thr Val Ser Ser
115

<210> SEQ ID NO 14
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

Gln Ser Val Leu Thr Gln Ser Ser Ser Ala Ser Gly Thr Pro Gly Gln
1 5 10 15

Thr Val Thr Val Ser Cys Ser Gly Ser Ser Ser Asp Ile Gly Ser Asn
20 25 30

Arg Val Asn Trp Tyr Gln Gln Leu Pro Gly Thr Ala Pro Lys Leu Leu
35 40 45

Ile Tyr Ser Asn Asp Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Ala Asp Glu Ala Asp Tyr Tyr Cys Ala Ala Trp Asp Asp Ser Leu
85 90 95

Ser Thr Tyr Val Phe Gly Ser Gly Thr Lys Val Thr Val Leu
100 105 110

<210> SEQ ID NO 15
<211> LENGTH: 836
<212> TYPE: PRT
<213> ORGANISM: Unknown
<220> FEATURE:
<223> OTHER INFORMATION: Description of Unknown: Periostin sequence

<400> SEQUENCE: 15

Met Ile Pro Phe Leu Pro Met Phe Ser Leu Leu Leu Leu Leu Ile Val
1 5 10 15

```
Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
```

-continued

```
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
            660                 665                 670

Ile Ile Thr Lys Val Val Glu Pro Lys Ile Lys Val Ile Glu Gly Ser
        675                 680                 685

Leu Gln Pro Ile Ile Lys Thr Glu Gly Pro Thr Leu Thr Lys Val Lys
    690                 695                 700

Ile Glu Gly Glu Pro Glu Phe Arg Leu Ile Lys Glu Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
            740                 745                 750

Arg Ile Ile Thr Gly Pro Glu Ile Lys Tyr Thr Arg Ile Ser Thr Gly
        755                 760                 765

Gly Gly Glu Thr Glu Glu Thr Leu Lys Lys Leu Leu Gln Glu Glu Val
    770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                805                 810                 815

Leu Gln Ala Asn Lys Lys Val Gln Gly Ser Arg Arg Arg Leu Arg Glu
            820                 825                 830

Gly Arg Ser Gln
        835
```

<210> SEQ ID NO 16

-continued

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 16

Ile Ser Ala Tyr Xaa Gly Asn Thr
1               5


<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 17

Asp Xaa Leu Val Val Pro Phe Asp Tyr
1               5


<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
1               5
```